US008232063B2

(12) United States Patent
Jorgensen et al.

(10) Patent No.: US 8,232,063 B2
(45) Date of Patent: *Jul. 31, 2012

(54) H+-GATED ION CHANNEL

(75) Inventors: Erik M. Jorgensen, Salt Lake City, UT (US); Asim A. Beg, Ann Arbor, MI (US); Paola Nix, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/211,898

(22) Filed: Aug. 17, 2011

(65) Prior Publication Data

US 2012/0029180 A1    Feb. 2, 2012

Related U.S. Application Data

(63) Continuation of application No. 12/905,647, filed on Oct. 15, 2010, now Pat. No. 8,012,702, which is a continuation of application No. 12/189,014, filed on Aug. 8, 2008, now Pat. No. 7,820,791, which is a continuation of application No. 11/587,018, filed as application No. PCT/US2005/013415 on Apr. 20, 2005, now abandoned.

(60) Provisional application No. 60/563,939, filed on Apr. 20, 2004.

(51) Int. Cl.
*G01N 33/53* (2006.01)
(52) U.S. Cl. ........................................ 435/7.2
(58) Field of Classification Search .................. None
See application file for complete search history.

(56) References Cited

U.S. PATENT DOCUMENTS

| 7,820,791 | B2 | 10/2010 | Jorgensen et al. | 530/350 |
|---|---|---|---|---|
| 8,012,702 | B2 | 9/2011 | Jorgensen et al. | 435/72 |
| 2003/0153519 | A1 | 8/2003 | Kay et al. | 514/44 |
| 2003/0175772 | A1 | 9/2003 | Wang | 453/321.1 |
| 2009/0183270 | A1 | 7/2009 | Adams et al. | 800/278 |

FOREIGN PATENT DOCUMENTS

WO    WO 2005/118640    12/2005

OTHER PUBLICATIONS

Beg AA, et al. (2003). EXP-1 is an excitatory GABA-gated cation channel. Nat Neurosci 6, 1145-1152.
Bertrand B, et al. (1994). The Na+/H+ exchanger isoform 1 (NHE1) is a novel member of the calmodulin-binding proteins. Identification and characterization of calmodulin-binding sites. J Biol Chem 269, 13703-13709.
Betz H. (1990). Ligand-gated ion channels in the brain: the amino acid receptor superfamily. Neuron 5, 383-392.
Brejc K, et al. (2001). Crystal structure of an ACh-binding protein reveals the ligand-binding domain of nicotinic receptors. Nature 411, 269-276.
Chalfie M, et al. (1994). Green fluorescent protein as a marker for gene expression. Science 263, 802-805.
U.S. Appl. No. 60/528,567, filed Dec. 10, 2003, Planelles et al.
U.S. Appl. No. 60/518,856, filed Nov. 10, 2003, Alvarado et al.
Counillon L, et al. (2000). The expanding family of eucaryotic Na(+)/H(+) exchangers. J Biol Chem 275, 1-4.
Croll NA. (1975). Behavioural analysis of nematode movement. Adv Parasitol 13, 71-122.
Dal Santo P, et al. (1999). The inositol trisphosphate receptor regulates a 50-second behavioral rhythm in *C. elegans*. Cell 98, 757-767.
Davies PA, et al. (2003). A novel class of ligand-gated ion channel is activated by $Zn^{2+}$. J Biol Chem 278, 712-717.
Engel AG, et al. (1996). New mutations in acetylcholine receptor subunit genes reveal heterogeneity in the slow-channel congenital myasthenic syndrome. Hum Mol Genet 5, 1217-1227.
Karlin A, et al. (1995). Toward a structural basis for the function of nicotinic acetylcholine receptors and their cousins. Neuron 15, 1231-1244.
Leonard RJ, et al. (1988). Evidence that the M2 membrane-spanning region lines the ion channel pore of the nicotinic receptor. Science 242, 1578-1581.
Liu DW, et al. (1994). Regulation of a periodic motor program in *C. elegans*. J Neurosci 14, 1953-1962.
Maruyama IN, et al. (1995). cRACE: a simple method for identification of the 5' end of mRNAs. Nucleic Acids Res 23, 3796-3797.
McIntire SL, et al. (1993a). Genes required for GABA function in *Caenorhabditis elegans*. Nature 364, 334-337.
McIntire SL, et al. (1993b). The GABAergic nervous system of *Caenorhabditis elegans*. Nature 364, 337-341.
Orlowski J, et al. (1997). $Na^+/H^+$ exchangers of mammalian cells. J Biol Chem 272, 22373-22376.
Ortells MO, et al. (1995). Evolutionary history of the ligand-gated ion-channel superfamily of receptors. Trends Neurosci 18, 121-127.
Palma A, et al. (1991). Effects of pH on acetylcholine receptor function. J Membr Biol 120, 67-73.
Pasternack, et al. (1992). Influence of extracellular and intracellular pH on GABA-gated chloride conductance in crayfish muscle fibres. Neuroscience 47, 921-929.
Thomas JH. (1990). Genetic analysis of defecation in *Caenorhabditis elegans*. Genetics 124, 855-872.
Treinin M, et al. (1995). A mutated acetylcholine receptor subunit causes neuronal degeneration in *C. elegans*. Neuron 14, 871-877.
Unwin N. (1993). Nicotinic acetylcholine receptor at 9 A resolution. J Mol Biol 229, 1101-1124.

(Continued)

*Primary Examiner* — Michael Pak
(74) *Attorney, Agent, or Firm* — Ballard Spahr LLP

(57) ABSTRACT

The invention relates to an isolated or recombinant $Na^+/H^+$ exchanger comprising an isolated or recombinant $Na^+/H^+$ exchanger, particularly to the PBO-4 $Na^+/H^+$ exchanger. Also disclosed is an isolated or recombinant protein component of an H+-gated channel which can be affected by extracellular $Ca^{2+}$ concentration. In particular, the invention relates to PBO-5 and/or PBO-8 and/or a H+-gated channel composed of PBO-5 and PBO-8. The invention relates to compounds isolated from a vertebrate organism, wherein said compounds comprise at least a part of a H+-gated channel or $Na^+/H^+$ exchanger. The invention also relates to a method for identifying a component of a H+-gated channel in a vertebrate organism.

5 Claims, 15 Drawing Sheets

OTHER PUBLICATIONS

Wakabayashi S, et al. (1994). Mutation of calmodulin-binding site renders the $Na^+/H^+$ exchanger (NHE1) highly H(+)- sensitive and $Ca^{2+}$ regulation-defective. J Biol Chem 269, 13710-13715.

Wakabayashi S, et al. (1997). Calmodulin-binding autoinhibitory domain controls "pH-sensing" in the $Na^+/H^+$ exchanger NHE1 through sequence-specific interaction. Biochemistry 36, 12854-12861.

Waldmann R, et al. (1997). A proton-gated cation channel involved in acid-sensing. Nature 386, 173-177.

Waldmann R, et al. (1999). H(+)-gated cation channels Ann N Y Acad Sci 868, 67-76.

*C. elegans* Sequencing Consortium. (1998) Genome sequence of the nematode *C. elegans*: a platform for investigating biology. Science 282(5396): 2012-2018.

Notice of Abandonment issued Mar. 24, 2009 for U.S. Appl. No. 11/587,018, which claims priority to PCT/US2005/013415 filed on Apr. 20, 2005 (Inventors: Jorgensen et al.) (1 page).

Preliminary Amendment filed Oct. 20, 2006 for U.S. Appl. No. 11/587,018, which claims priority to PCT/US2005/013415 filed on Apr. 20, 2005 (Inventors: Jorgensen et al.) (7 pages).

Issue Notification issued Oct. 6, 2010 for U.S. Appl. No. 12/189,014, filed Aug. 8, 2008 (Inventors: Jorgensen et al.) (1 page).

Response to Rule 312 Communication issued Sep. 2, 2010 for U.S. Appl. No. 12/189,014, filed Aug. 8, 2008 (Inventors: Jorgensen et al.) (3 pages).

Interview Summary issued Sep. 2, 2010 for U.S. Appl. No. 12/189,014, filed Aug. 8, 2008 (Inventors: Jorgensen et al.) (3 pages).

Examiner-Initiated Interview Summary with Examiner's Amendment issued Jul. 22, 2010 for U.S. Appl. No. 12/189,014, filed Aug. 8, 2008 (Inventors: Jorgensen et al.) (5 pages).

Amedment After Allowance Pursuant to 37 C.F.R. § 1.132 and M.P.E.P. § 714.16 filed Jul. 21, 2010 for U.S. Appl. No. 12/189,014, filed Aug. 8, 2008 (Inventors: Jorgensen et al.) (3 pages).

Notice of Allowance and Fee(s) Due issued Jun. 25, 2010 for U.S. Appl. No. 12/189,014, filed Aug. 8, 2008 (Inventors: Jorgensen et al.) (6 pages).

Notice of Allowance and Fee(s) Due issued Dec. 30, 2009 for U.S. Appl. No. 12/189,014, filed Aug. 8, 2008 (Inventors: Jorgensen et al.) (8 pages).

Amendment and Response filed Mar. 24, 2009 for U.S. Appl. No. 12/189,014, filed Aug. 8, 2008 (Inventors: Jorgensen et al.) (8 pages).

Issue Notification issued Aug. 17, 2011 for U.S. Appl. No. 12/905,647, filed Oct. 15, 2010 (Inventors: Jorgensen et al.) (1 page).

Notice of Allowance and Fee(s) Due with Examiner Interview Summary issued Apr. 28, 2011 for U.S. Appl. No. 12/905,647, filed Oct. 15, 2010 (Inventors: Jorgensen et al.) (8 pages).

Preliminary Amendment filed Ocdtober 15, 2010 for U.S. Appl. No. 12/905,647, filed Oct. 15, 2010 (Inventors: Jorgensen et al.) (6 pages).

International Search Report and Written Opinion issued Mar. 28, 2006 for PCT/US2005/013415 filed on Apr. 20, 2005 and later published as WO2005/118640 on Dec. 15, 2006 (Inventors: Jorgensen et al.; Applicant: University of Utah Research Foundation) (6 pages).

International Preliminary Report on Patentability issued Oct. 25, 2006 for PCT/US2005/013415 filed on Apr. 20, 2005 and later published as WO2005/118640 on Dec. 15, 2006 (Inventors: Jorgensen et al.; Applicant: University of Utah Research Foundation) (4 pages).

H+-GATED ION CHANNEL

CROSS-REFERENCE TO RELATED APPLICATIONS

This application is a continuation of application Ser. No. 12/905,647 filed on Oct. 15, 2010 now U.S. Pat. No. 8,012,702, which is a continuation of application Ser. No. 12/189,014 filed on Aug. 8, 2008 (now U.S. Pat. No. 7,820,791), which is a continuation of application Ser. No. 11/587,018 (now abandoned), which is a National Phase Application of International Application No. PCT/US2005/013415, filed Apr. 20, 2005, which claims priority to U.S. Provisional Application No. 60/563,939, filed Apr. 20, 2004, the entirety of which is incorporated herein by reference.

STATEMENT REGARDING FEDERALLY SPONSORED RESEARCH

This invention was made with government support under Grant MH60997-02 awarded by the National Institute of Health. The government has certain rights in the invention.

TECHNICAL FIELD

This invention relates to biotechnology, more particularly to one or more members of the "cys-loop" ligand-gated ion channel superfamily, which are activated by a proton and/or $H^+/Na^+$ exchange proteins, and methods of using the same.

BACKGROUND

Motor behaviors such as locomotion rely on precise signaling from the nervous system to coordinate various muscle activities. The neuromuscular junction has been extensively studied and a considerable amount of information exists on how information is communicated across the synapse between a motor neuron and a muscle cell. At the cellular level, depolarization of the motor neuron produces an action potential that is propagated to the presynaptic terminal Depolarization causes the opening of voltage-gated calcium channels at the presynaptic terminal, resulting in an increase in intracellular calcium. In response to local increases in calcium, neurotransmitter filled vesicles fuse with the presynaptic plasma membrane, releasing their contents into the synaptic cleft. Postsynaptic ligand-gated ion channels on the muscle bind the neurotransmitter, resulting in the opening of an integral ion channel. Depending on an ion channel's permeability, the muscle is either hyperpolarized or depolarized.

Chemical synaptic transmission mediates fast and slow communication between cells, but it is not the only means of communication within the nervous system. Signals may also be conveyed nonsynaptically. In this case, a neurotransmitter or hormone is released at one site and slowly diffuses to distant target sites that are not in contact with the original site of release. This type of signaling is more suited to global, modulatory activities rather than functions requiring a rapid response. The interplay of synaptic and non-synaptic communication ultimately determines how a nervous system mediates particular behaviors.

In *C. elegans*, synaptic transmission has been extensively studied at the genetic, cellular and molecular levels. Most behaviors in the worm follow a simple paradigm in which information is directed from the sensory neurons to motor neurons to muscle, via synaptic contacts. However, the defecation cycle in *C. elegans* is a unique behavior in that it appears to be mediated by both synaptic, as well as nonsynaptic transmission (McIntire et al., 1993b; Thomas, 1990). Defecation in *C. elegans* is a stereotyped behavior that occurs every 50 seconds for the life of the animal, and is characterized by the coordinated activation of three independent muscle contractions (Croll, 1975; Thomas, 1990). The cycle is initiated with a posterior body contraction, followed by an anterior body contraction and finalized by an enteric muscle contraction, which expels intestinal contents. A simplified genetic pathway to explain the defecation behavior was proposed by Jim Thomas (Thomas, 1990) (see, FIG. 1B). In this model, a clock mechanism keeps time independently of the motor program. At the appropriate interval, the clock first signals the posterior body contraction and then signals the common anterior body and enteric muscle contraction mechanism, which ultimately leads to activation of the individual muscle contractions (Liu and Thomas, 1994; Thomas, 1990) (FIG. 1B).

To determine the cellular basis of the defecation motor program, extensive cellular laser ablations have been performed. Based on these studies the motor neurons AVL and DVB were demonstrated to mediate the anterior body and enteric muscle contraction, but not posterior body contraction (McIntire et al., 1993b). The anterior body contraction is mediated by the motor neuron AVL, but the neurotransmitter that mediates this contraction is unknown (see, FIG. 1A). While AVL alone is required for anterior body contraction, both the AVL and DVB motor neurons serve a redundant function in activating the enteric muscles (see, FIG. 1A). Activation of the enteric muscles is GABA-dependent and is mediated by the EXP-I receptor (Beg and Jorgensen, 2003; McIntire et al., 1993a; McIntire et al, 1993b).

Interestingly, no known neurons are required to maintain the clock or initiate the posterior body contraction, suggesting that cycle timing and posterior body contraction are mediated by a non-neuronal mechanism (Liu and Thomas, 1994; McIntire et al., 1993b; Thomas, 1990) (see, FIG. 1A). Furthermore, mutations that disrupt classical neurotransmission and secretion do not affect the posterior body contraction. Taken together, these data suggest that posterior body contraction occurs through a non-neuronal mechanism that does not rely on classical or peptidergic neurotransmission.

Many genes have been identified that affect only specific aspects of the defecation motor program. It has been demonstrated that timekeeping of the cycle is controlled by an endogenous clock that resides in the intestine (Dal Santo et al., 1999). The cycle time is set by the activity of the itr-1 gene, which encodes an inositol triphosphate (IP3) receptor which mediates release of calcium from the smooth endoplasmic reticulum into the intestine every 50 seconds (Dal Santo et al., 1999). Mutations in the itr-1 gene slow down or eliminate the cycle, while overexpression accelerates the cycle. In the intestine, calcium levels oscillate with the same period as the defecation cycle (50 seconds) and peak calcium levels immediately precede the posterior body contraction (Dal Santo et al., 1999). Therefore, the frequency of intracellular calcium release in the intestine, determines the frequency of the defecation cycle.

It has been demonstrated that there is a one-to-one relationship between the calcium spike in the intestine and the execution of the posterior body contraction (Dal Santo et al., 1999). Normally, motor behaviors such as muscle contraction are mediated by the nervous system. Since neuronal input is not required to initiate the posterior body contraction, these muscles could be directly activated by a $Ca^{2+}$ regulated signal from the intestine.

BRIEF SUMMARY

In accordance with the purpose of this invention, as embodied and broadly described herein, this invention relates to an isolated or recombinant Na$^+$/H$^+$ exchanger comprising an isolated or recombinant Na$^+$/H$^+$ exchanger. The invention further relates to the PBO-4 Na$^+$/H$^+$ exchanger and Na$^+$/H$^+$ exchangers having at least 80%, 81%,82%, 83%, 84%, 85%, 86%, 87%, 88%, 89%, 90%, 91%, 92%, 93%, 94%, 95%, 96%, 97%, 98%, and/or 99% identity to PBO-4 (SEQ ID NO:8). Optionally, the isolated or recombinant Na$^+$/H$^+$ exchanger functions in the intestine.

The invention also relates to isolated or recombinant protein component of an H$^+$-gated channel. The invention further relates to a H$^+$-gated channel that is effected by extracellular Ca$^{2+}$ concentration. In particular, the invention relates to PBO-5 (SEQ ID NOs: 1 and 2) and/or PBO-8 (SEQ ID NOs: 3-5) and/or a H$^+$-gated channel composed of PBO-5 and PBO-8. In addition the invention relates to isolated and/or recombinant proteins having at least 80%, 81%, 82%, 83%, 84%, 85%, 86%, 87%, 88%, 89%, 90%, 91%, 92%, 93%, 94%, 95%, 96%, 97%, 98%, and/or 99% identity to PBO-5 and/or PBO-8. Further, the invention relates to a H$^+$-gated channel that is pH sensitive. The invention further relates to a H$^+$-gated cation channel.

The invention relates to compounds isolated from a vertebrate organism, wherein said compounds comprise at least a part of a H$^+$-gated channel or Na$^+$/H$^+$ exchanger. The invention further relates to a Na$^+$/H$^+$ exchanger identified in a vertebrate organism.

The invention also relates to a method for identifying a component of a H$^+$-gated channel in a vertebrate organism. For example, by screening a vertebrate organism for the presence of a component of a H$^+$-gated channel; identifying the component of the H$^+$-gated channel; and confirming that the component of the H$^+$-gated channel is a component of said H$^+$-gated channel. Optionally, the method further comprises isolating the component of said H$^+$-gated channel.

The invention also relates to screening a component of a H$^+$-gated channel for activation or inhibition by a candidate drug. The invention also relates to screening the component of a H$^+$-gated channel for binding to HEPES and/or identifying mutations which prevent binding to HEPES.

The invention further relates to a protein produced by a process of screening a vertebrate organism for the presence of a component of a H$^+$-gated channel; identifying said component of said H$^+$-gated channel; and confirming that said component of said H-gated channel is a component of said H$^+$-gated channel.

The invention further relates to compounds according to the invention identified in a mammal.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1A is a schematic drawing of the defecation cycle. Every 50 seconds a cycle is initiated by the posterior body contraction (pBoc), followed by an anterior body contraction (aBoc), and completed by an enteric muscle contraction, (Emc), which mediates expulsion of intestinal contents. Listed to the right are the motor neurons and neurotransmitters involved in each muscle contraction. FIG. 1B illustrates the genes involved and their affects on the cycle. A 50 second clock independently keeps time of the cycle. Each step of the defecation cycle can be specifically affected by mutation, demonstrating that cycle timing and muscle activation do not rely on one another. Muscle activation of each step occurs independently of the others. However, the anterior body contraction and the enteric muscle contraction share a common mechanism upstream of muscle activation.

FIG. 4(A) shows the exon-intron structure of pbo-8. The pbo-8 locus consists of 13 exons that span 4.1 kb of the genome. FIG. 4(B) illustrate that PBO-5 and PBO-8 represent novel ligand-gated ion channel subunits. The PBO-5 and PBO-8 subunits cannot be categorized into one of the four ligand-gated ion channel families based on sequence analysis. Alignments were performed using clustal X and the bootstrap method with 'neighbor-joining' search was used to create the tree. Bootstrap values of 1,000 replicates are indicated on the tree.

FIGS. 5A and 5B are confocal images of animals expressing an integrated pbo-5:: gfp fusion gene. The animals are oriented with anterior to the left, and posterior to the right. GFP expression is observed in the most posterior muscle cells (FIG. 5A) and in the neurons RIFL, RIFR, and RIS (FIG. 5B). FIG. 5C is a schematic drawing to illustrate pbo-5 expression within the context of the entire animal.

FIG. 8A shows the current-voltage (I-V) relationship of PBO-5/PBO-8 ion channels. The reversal potential determined under control conditions was 10.18±0.80 mV (n=13). Inset, representative traces of an experiment. Note, the strong inward rectification of PBO-5/PBO-8 receptors. FIG. 8B shows $Na^+$ permeability. Na ions were replaced with the cation NMDG, in $Na^+$ free Ringer's. There is a negative shift in reversal potential ($E_{rev}$=−82.90±8.13 mV (n=6)) and the inward current in nearly abolished which suggests that Na is the primary charge carrier through the PBO-5/PBO-8 channel. FIG. 8C shows $Cl^-$ permeability. Chloride ions were replaced with the anion gluconate, in $Cl^-$ free Ringer's. The negligible shift in reversal potential demonstrates that chloride ions do not underlie the ionic conductance through PBO-5/PBO-8 channels ($\Delta E_{rev}$=0.25 mV, P>0.05, two-way ANOVA, (n=8)).

FIG. 8D shows $K^+$ permeability. Replacement of $K^+$ for $Na^+$ in the extracellular solution demonstrates PBO-5/PBO-8 ion channels discriminate poorly between monovalent cations. Note the inward current is still present and there was not significant shift in reversal potential compared to control (P>0.05; two-way ANOVA, (n=4), demonstrating PBO-5/PBO-8 is a nonselective cation channel.

FIG. 9A shows the current-voltage (I-V) analysis of PBO-5/PBO-8 receptors under different $Ca^{2+}$ concentrations. Reversal potentials were measured under 1 mM $Ca^{2+}$ control and 3 mM and 10 mM test $Ca^{2-}$ conditions. Increasing extracellular $Ca^{2+}$ caused a positive shift in reversal potentials suggesting $Ca^{2+}$ is permeable to PBO-5/PBO-8 channels. Note the decreased inward current as extracellular Ca increased. FIG. 9B shows $Ca^{2+}$ permeability in $Na^+$ free Ringers. To better resolve $Ca^{2+}$ permeability, the I-V relationships where $Ca^{2+}$ was the only relevant extracellular ion were determined. These data demonstrate PBO-5/PBO-8 ion channels are $Ca^{2+}$ permeable.

FIG. 10A shows the results of normalized current amplitude versus test pH at four different extracellular $Ca^{2+}$ concentrations. Increasing $Ca^{2+}$ decreases the pH necessary for half-maximal activation. Currents were normalized to the maximal value at pH 6.0 for each $[Ca^{2+}]_o$ condition. FIG. 10B shows that a normalized current amplitude of test pH evoked responses at three $Ca^{2+}$ concentrations. $Ca^{2+}$ shifts activation but increasing extracellular does not affect maximal activation. Current were normalized to the value at 1 mM $Ca^{2+}$ for each pH tested.

FIG. 12 illustrates the genetic mapping and molecular cloning of pbo-4.

Figure 13:
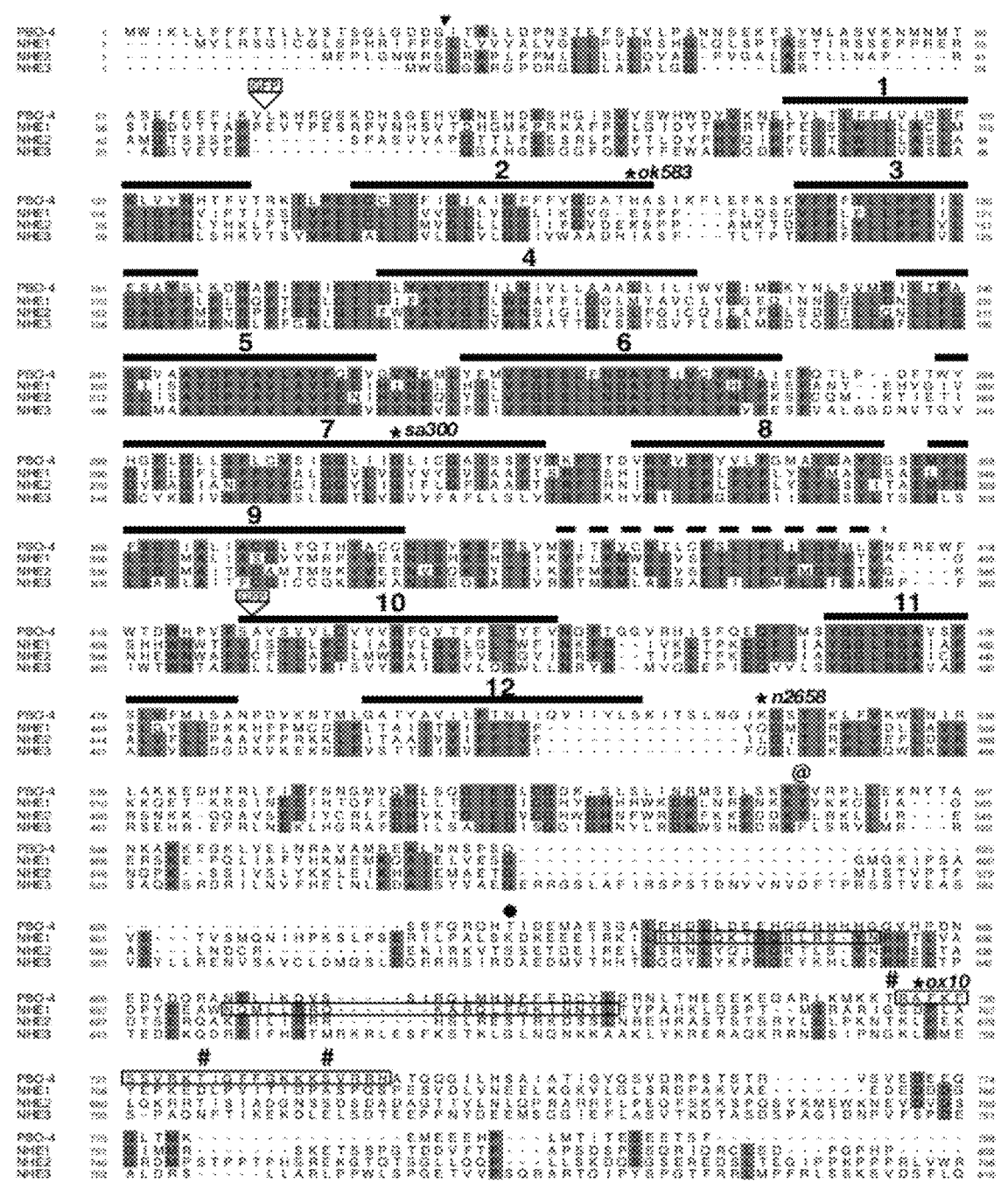

FIG. 13 shows a sequence alignment of PBO-4 to human $Na^+/H^+$ exchangers. Deduced polypeptide sequence of PBO-4 aligned with human NHE1(P19634), NHE2 (Q9UBY0) and NHE3(P48764) are shown. Sequences were aligned with ClustalX tities are shaded and the arrowhead indicates the predicted signal peptide cleavage site. The last translated amino acid of each pbo-4 mutant allele is denoted by a star. The black bars indicate predicted transmembrane domains, and the dotted line denotes the re-entrant loop as determined for NHE1. The boxed sequence indicates the predicted calmodulin binding domain. The positions of the GFP insertions are indicated by triangles.

DETAILED DESCRIPTION

Figure 1:
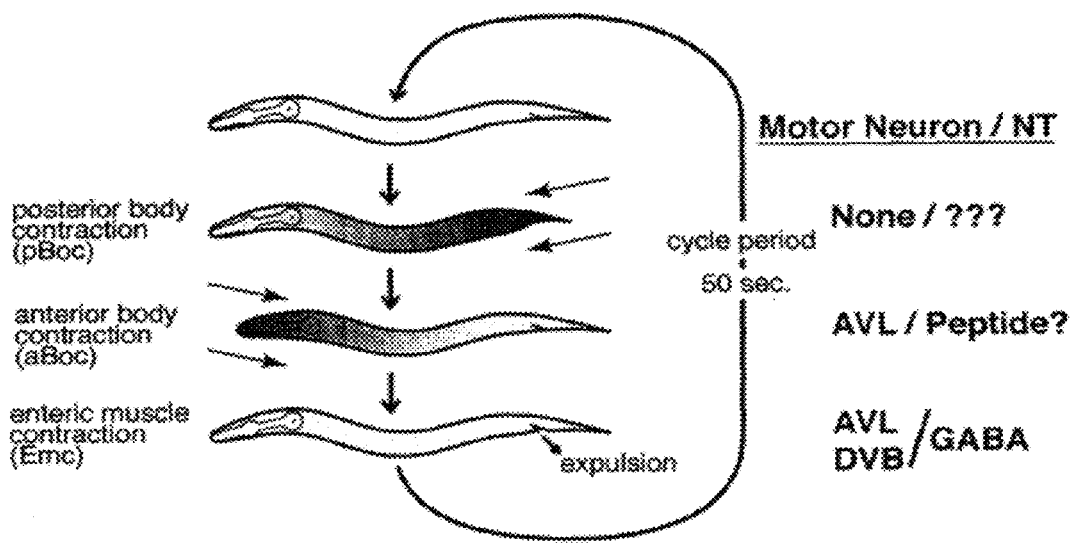
FIG. 1 illustrates the defecation cycle behavior and genetics of the defecation cycle in C. elegans.
Figure 1:
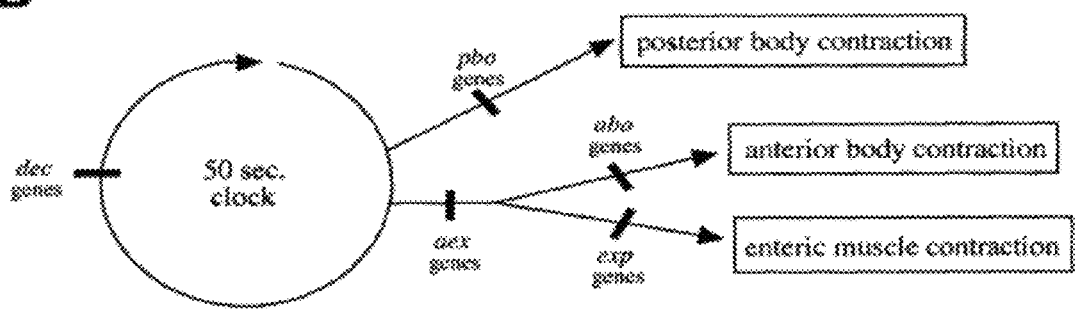

As used herein and in the appended claims, the singular forms "a", "an", and "the" include plural reference unless the context clearly dictates otherwise. For example, reference to "a host cell" includes a plurality of such host cells.

As used herein a "Substantially Identical" polypeptide sequence means an amino acid sequence which differs from a reference sequence only by conservative amino acid substitutions, for example, substitution of one amino acid for another of the same class (for example, valine for glycine, arginine for lysine, etc.) or by one or more non-conservative substitutions, deletions, or insertions located at positions of the amino acid sequence which do not destroy the function of the polypeptide (assayed, for example, as described herein). Preferably, such a sequence is at least 80-100%, more preferably at least 85%, and most preferably at least 90% substantially identical at the amino acid level to the sequence used for comparison.

To identify the nature of the signal, source, and target, screens for mutations affecting the defecation cycle and in particular, mutations specifically affecting the posterior body contraction have been performed. From these screens, only three genes, pbo-1, pbo-4 and pbo-5 result in a specific loss of posterior body contraction, without affecting any other aspect of the defecation motor program. The pbo-1 gene has not been cloned. The pbo-4 gene encodes a putative $Na^+/H^+$ exchanger and is required for activation of the posterior body contraction (P. Dal Santo, personal communication; see Discussion). Its expression in the posterior intestine suggests that pbo-4 functions as a mediator between the calcium signal of the clock in the intestine and the muscle receptor that stimulates the posterior body contraction.

$Na^+/H^+$ exchangers have been implicated in numerous physiological processes such as intracellular pH homeostasis, cell volume regulation, and reabsorption of NaCl across epithelial cells. However, the proton can be involved in more complex cellular processes other than intracellular pH regulation. Deletion of genes involved in $H^+$ secretion and reception results in a broad range of cellular and behavioral phenotypes. Significantly, deletion of the murine NHE1 gene reveals it is required for functions as diverse as pH homeostasis to cell morphology and adhesion. Consistent with a broader role for protons as intercellular messengers, a large family of proton-gated channels, termed the acid-sensing ion channels (ASICs), have been identified. Knockouts of specific ASIC family members have demonstrated that proper $H^+$ signaling is required not only for sensory modalities such as nociception and mechanoreception, but also for synaptic plasticity and learning and memory in the brain. While specific $H^+$-gated receptors such as ASIC1 are expressed in hippocampal neurons, the source of protons required to activate these receptors remains a mystery. Hence, the present invention is useful in the field of medicine and provides valuable research tools for the identification of medical and veterinary compounds.

The gene pbo-5 gene encodes a novel $H^+$-gated ion channel subunit. When expressed in *Xenopus oocytes*, PBO-5 co-assembles with the PBO-8 subunit to form a functional $H^+$-gated nonselective cation channel. PBO-5 and PBO-8 are expressed in the posterior body wall muscles, suggesting these two subunits are localized to the appropriate tissues to mediate posterior body contraction. The channel encoded by PBO-5/8 is an inwardly-rectifying non selective cation channel. The molecular identification of the PBO-5 and PBO-8 receptor subunits defines a unique class of the cys-loop ligand-gated ion channel superfamily, and demonstrates a non-neuronal signaling mechanism. Furthermore, the functional characterization of $H^+$ sensitivity demonstrates that the PBO-5/8 signaling pathway defines a novel mechanism of cellular communication that relies on $H^+$ as a physiological transmitter.

Methods

Molecular Characterization of pbo-5 and pbo-8

The sequence of the pbo-5 transcript was determined by reverse transcription of wild-type RNA followed by PCR amplification (RT-PCR) and direct sequencing. The 5' trans-spliced sequence was obtained by PCR amplification using an SL1 primer and a nested, gene specific primer in the second exon. The 3' sequence was obtained by PCR amplification with nested primers in the third predicted exons and with an oligo-dT primer. PCR products were cloned into the pCR2.1 TA cloning vector (Invitrogen) and a full length clone pPD68 was generated.

PBO-8 cDNAs were isolated by RT-PCR. We determined the 5' end of the gene by circular RACE (Maruyama et al., 1995). The 3' end of the gene was based on computer prediction and sequence similarity to PBO-5. To isolate full-length cDNAs, oligonucleotide primers were designed to the 5' and 3' untranslated regions of pbo-8. PCR products were cloned into pCR2.1, and subsequent products were sequenced to generate a full-length error free PBO-8 cDNA.

Electrophysiology of PBO-5 and PBO-8

To generate plasmid constructs for *Xenopus oocyte* expression, the foil length error-free cDNA was subcloned into the pSGEM expression vector (courtesy M. Hollmann). The pbo-5 expression vector was constructed by cutting the pPD70 plasmid with restriction enzymes SacII and EagI, then using T4 DNA polymerase to blunt the ends. Cut products were gel purified (Qiagen) and re-ligated using T4 DNA ligase (Promega) to create the plasmid pAB20. The PBO-8 expression construct was made by cutting a previously sequenced error-free cDNA (M. Peter, unpublished). The cDNA was first cloned into the pSGEM expression vector. Next, the restriction enzymes SacII and BsaBI were used to cut the plasmid, and the ends were blunted with T4 DNA polymerase. Cut products were gel purified and re-ligated to produce pAB21.

Capped RNA was prepared using the T7 mMessage mMachine kit (Ambion). *Xenopus oocytes* were collected and coinjected with 25 ng each of PBO-5 and PBO-8 cRNA and two-electrode voltage clamp recordings were performed 3-5 days post-injection. The standard bath solution for dose-response and control I-V experiments was Ringer's (in mM): 115 NaCl, 1.8 BaCl2, 10 Bis-Tris Propane (pH 7.4 Acetic acid). For dose-response experiments, each oocyte was subjected to a 5 second application of test pH (7.0 - 5.0) with 2 minutes of pH 7.4 wash between test applications.

Ion selectivity experiments: All points are responses to test pulse applications of pH 6.8 for 5 seconds. The reversal potential of PBO-5/PBO-8 expressing oocytes were first determined in standard Ringer's (in mM): 115 NaCl, 1.0 CaCl2, 10 Bis-Tris Propane (pH 7.4, acetic acid). For chloride permeability a simplified solution was used, chloride-free (in mM): 115 $Na^+$ gluconate, 1.0 $CaCl_2$, 10 Bis-Tris Propane (pH 7.4 acetic acid). For $Na^+$ permeability a simplified solution was used, $Na^+$ free (in mM): 115 mM N-methyl D-glucamine (NMDG), 1.8 $CaCl_2$, 10 Bis-Tris Propane (pH 7.4 acetic acid)). All solutions were brought to pH by addition of NaOH or acetic acid. To determine $K^+$ permeability, I-V experiments were performed in $K^+$ Ringer's (in mM): 115 $K^+$-gluconate, 1.0 $CaCl_2$, 10 Bis-Tris Propane (pH=7.4 acetic acid). To determine $Ca^{2+}$ permeability extracellular $Na^+$ was lowered to 90 mM and extracellular $CaCl_2$ was increased to 3 mM and 10 mM, compare to 1 mM $Ca^{2+}$ control. To better resolve calcium permeability, the $Na^+$ free solution was used except $CaCl_2$ was increased ten-fold, 18 mM CaCl2 (in mM): 115 NMDG, 18 $CaCl_2$, 10 Bis-Tris Propane, (pH 7.4 acetic acid). Osmolarity was measured for each solution and was maintained at 240 mOsm by the addition of sucrose. All recordings were done at room temperature. We used 3M KCl filled electrodes with a resistance between 1-3 M$\Omega$. We used a 3M KCl agar bridge to minimize liquid junction potentials, and all liquid junctions potentials arising at the tip of the recording electrode were corrected online.

Data analysis. Data acquisition and analysis were performed using Axograph (Axon Instruments) software, and curve fitting and statistical analysis were performed with Prism (Graphpad). Dose-response curves from individual oocytes were normalized to the maximum and minimum values and averaged for at least eleven oocytes. Normalized data were fit to the four-parameter equation derived from the Hill equation: $Y=Min+(Max-Min)/(1+10(Log\ EC50-X)(nH))$, where Max is the maximal response, Min is the response at the lowest drug concentration, X is the logarithm of agonist concentration, EC50 is the half-maximal response, and nH is the Hill coefficient. Error bars represent the standard error of the mean.

Reversal potential values represent averaged linear regression measurements of individual experiments above and below the point of X-axis intersection. Because the PBO-5/PBO-8 receptor exhibits rectification we used linear regression from $-15$ to $+15$, where the relationship is most linear, to determine the reversal potential. Error bars represent the standard error of the mean.

Results pbo-5 Behavioral Analysis

Recessive alleles in the pbo-5 gene result in a strong posterior body contraction defective (Pbo) phenotype. The posterior body contraction is completely absent from these mutants while the other aspects of defecation such as anterior body contraction, enteric muscle contraction, and cycle timing remain unaffected. Other behaviors including locomotion, egg laying, feeding and mating are also normal.

In contrast to the recessive pbo-5 alleles, two dominant mutations, n2331 and ox7, result in a distinctive hypercontracted phenotype known as posterior body cramp. Specifically, when the defecation cycle is initiated in these mutants, the posterior body muscles contract but fail to immediately relax, and the enteric muscle contraction occurs while the posterior body wall muscles are still contracted. As the animals move, the posterior body muscles eventually relax and the next cycle can be observed.

pbo-5 Cloning

Figure 2:
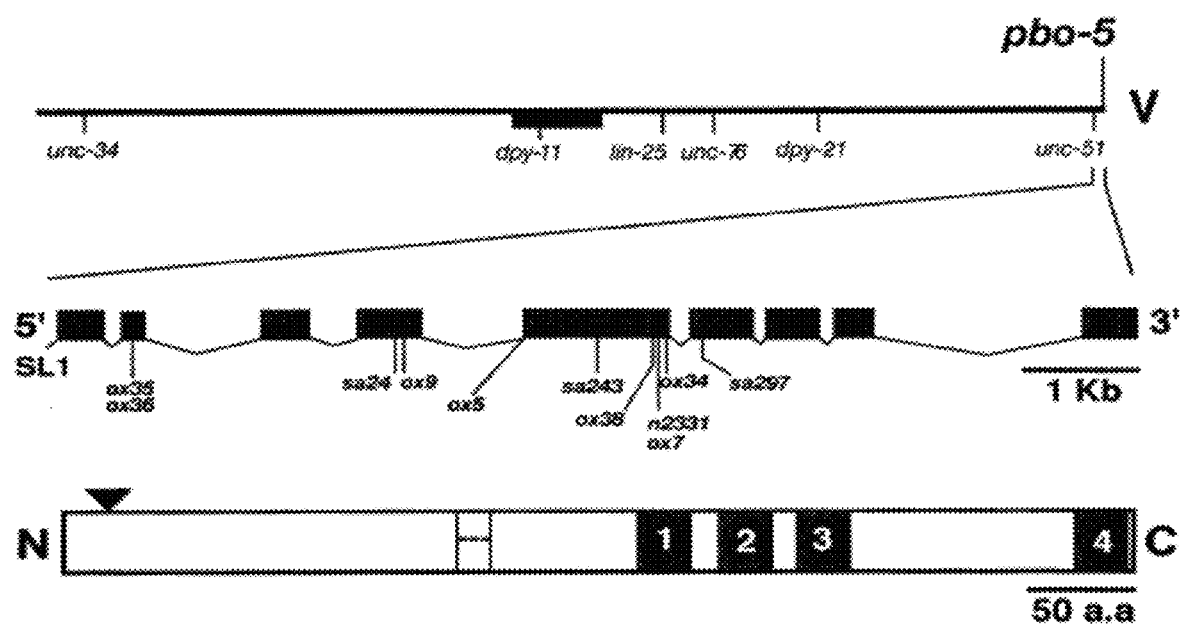
FIG. 2 illustrates the structure and molecular cloning of pbo-5. The genomic location of pbo-5 is the last predicted gene on chromosome V, approximately 1.2 kb from the telomere. The middle of FIG. 2 illustrates the exon-intron structure of the pbo-5 gene. Positions of mutations in pbo-5 alleles are shown below the predicted protein structure. Triangles represent the peptide signal, the dotted line is the disulfide-bond, the transmembrane domains are labeled 1-4.
Figure 3A:
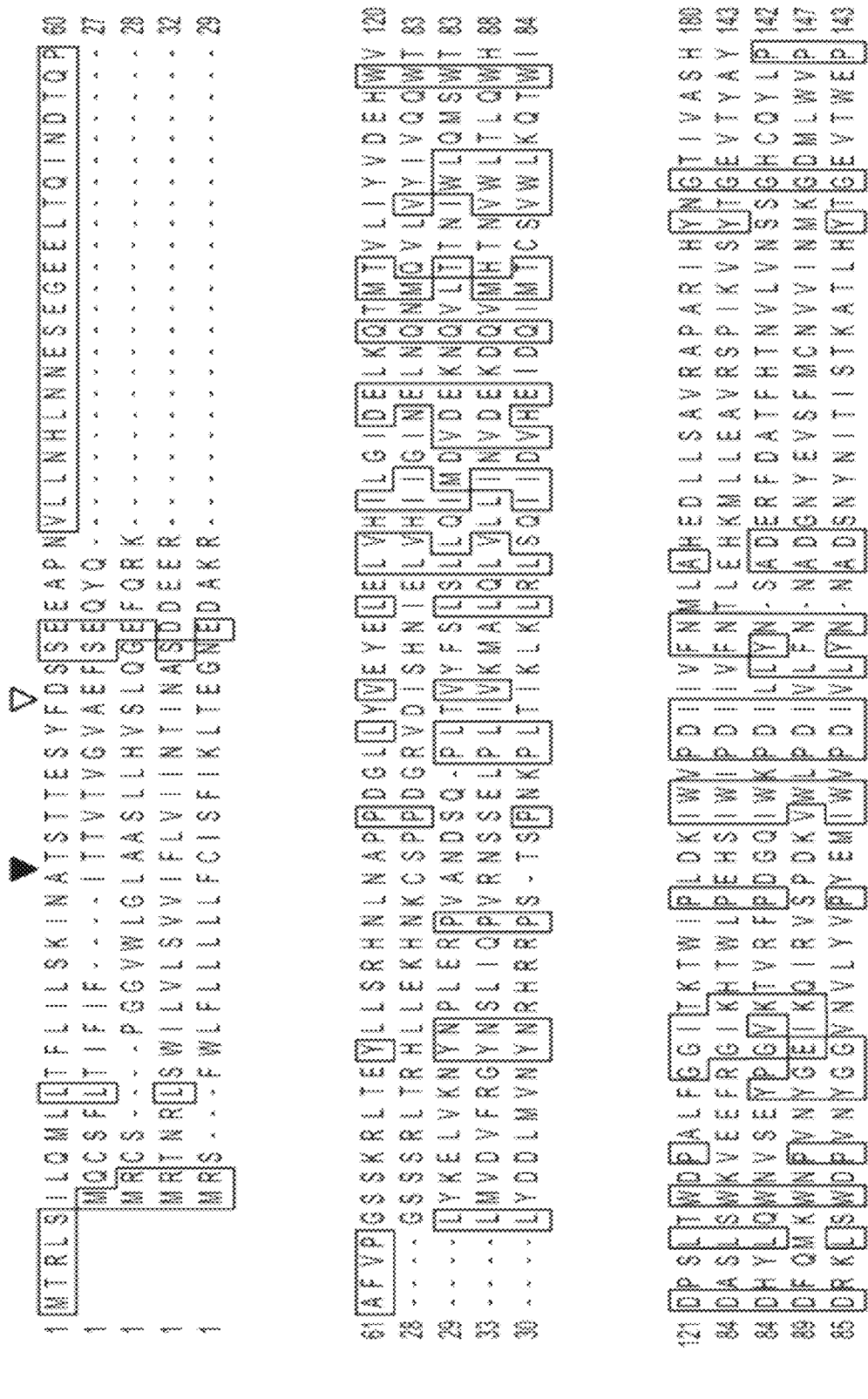
FIG. 3 shows the sequence alignment of PBO-5 and cholinergic subunits. The amino acid sequence for C. elegans PBO-5, PBO-8 (F11C7.1; SEQ ID NO:5), UNC-29, UNC-38, and human alpha 7 nicotinic acetylcholine receptors subunits. Sequences were aligned using clustal X and identities are shaded and boxed. The black and hollow filled triangles denote the signal peptide sequence for PBO-5 and PBO-8, respectively. The dotted line shows the invariant disulfide bond present in all ligand-gated ion channels. Black bars denote the four transmembrane domains.
Figure 3B:
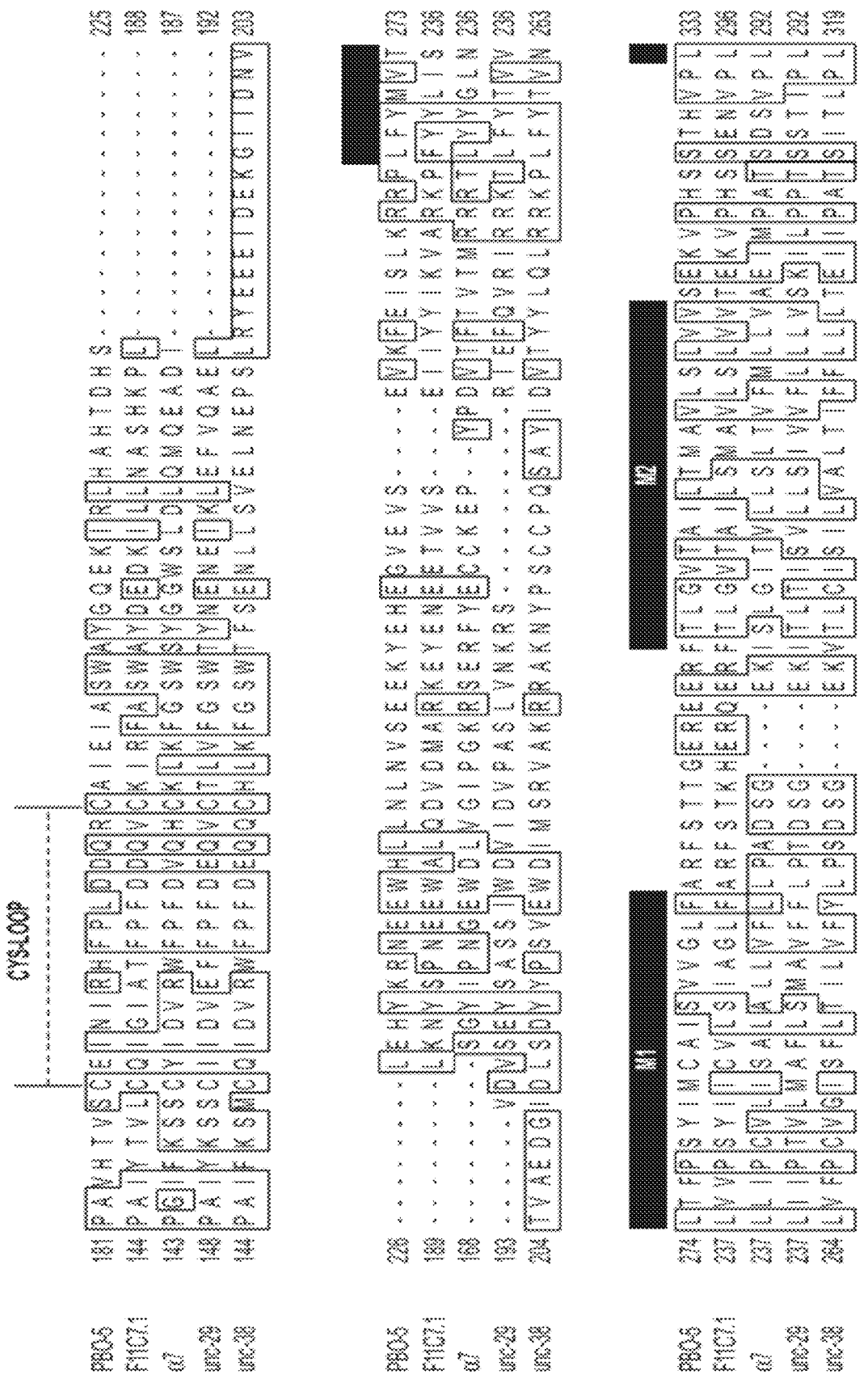
Figure 3C:
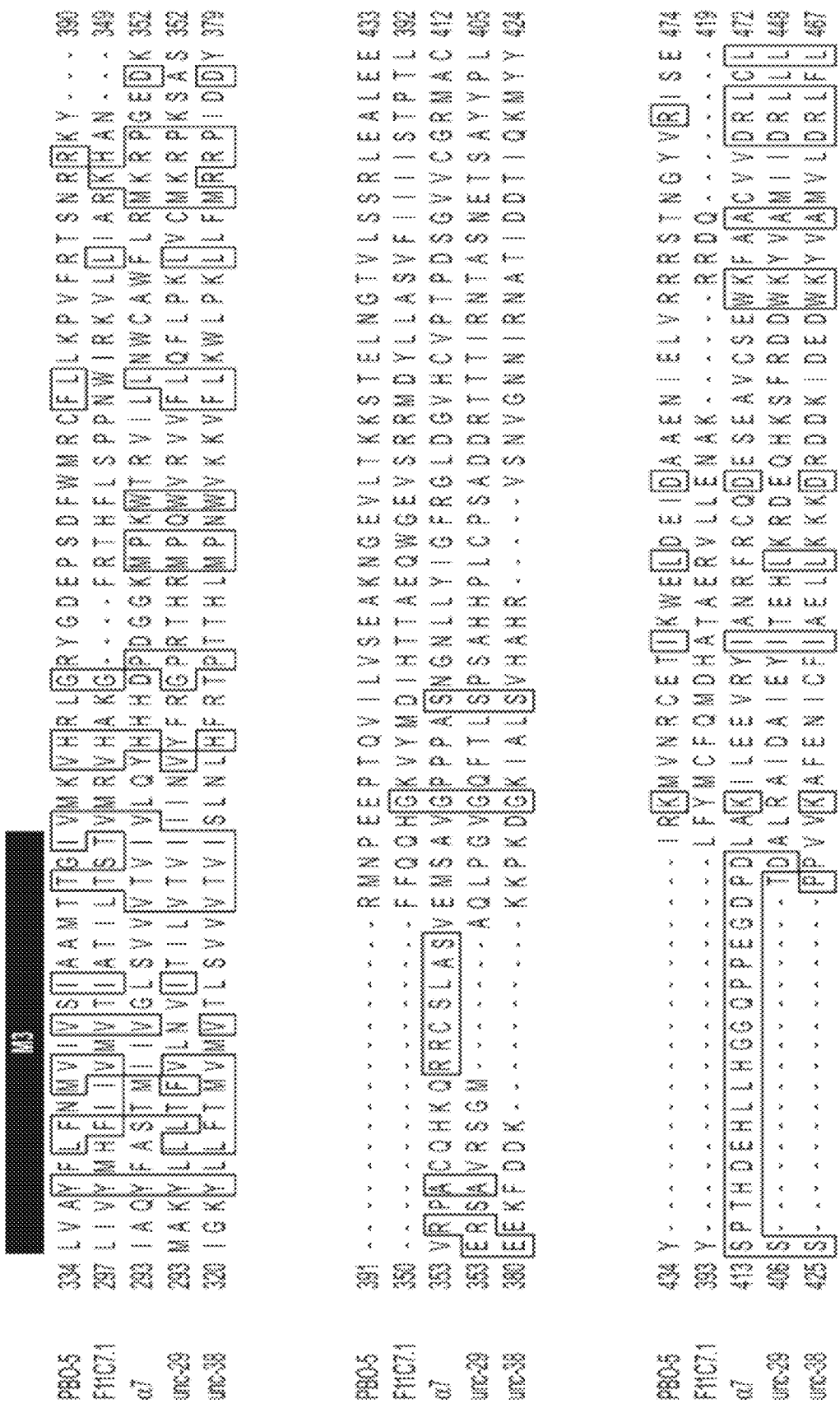
Figure 3D:
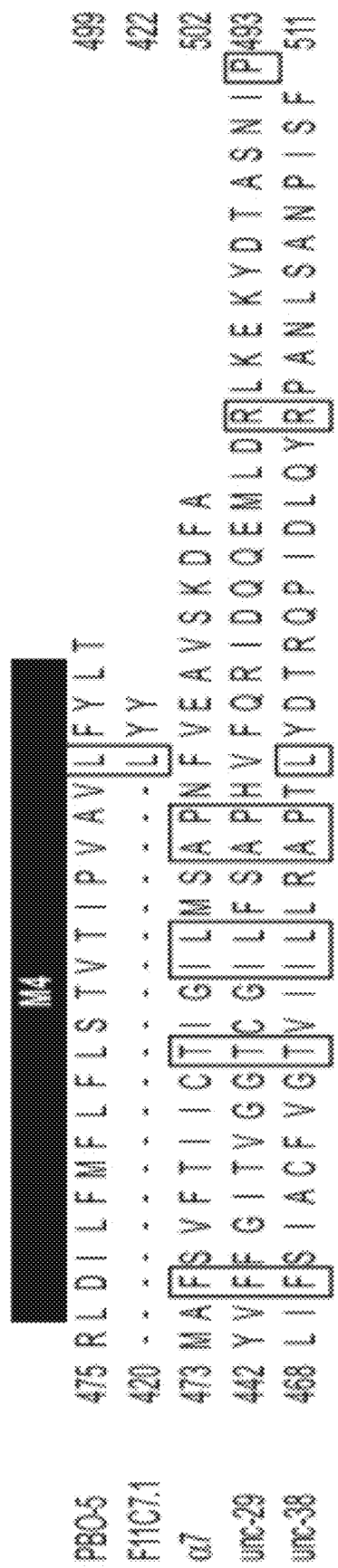

The pbo-5 gene was mapped to the right arm of chromosome V and cloned (FIG. 2). The Y44AE predicted open reading frame encodes pbo-5, confirmed by mutant allele sequencing (Table 1). Furthermore, a mini-gene construct containing the pbo-5 cDNA fused to 4.4 kb of sequences upstream of the second exon rescues the phenotype of pbo-5 (ox24) mutants.

TABLE 1 pbo-5 mutations

| Allele | Mutation | Protein | Exon/Domain |
|---|---|---|---|
| ox35 | Nonsense | Q 59 stop | 2 |
| ox36 |  | Q 59 stop | 2 |
| sa243 | ↓ | W 235 stop | 5 |
| N2331dm | Missense | L 316 F | 5(M2) |
| ox7dm |  | L 316 F | 5(M2) |
| ox38 |  | T 304 I | 5(M2) |
| ox34 |  | P 325 L | 5 (M2-M3 loop) |
| sa297 |  | M 342 T | 6 (M3) |
| ox9 |  | H 184 Q | 4 (LBD) |
| sa242 | ↓ | P 181 L | 4 (LBD) |
| ox5 | Splice |  | Intron 4 |
| n2330 | Deletion |  |  |
| ox4 |  |  |  |
| ox24 |  |  |  |
| ox26 |  |  |  |
| ox27 |  |  |  |
| ox30 |  |  |  |
| ox32 |  |  |  |
| ox39 | ↓ |  |  | pbo-5 Encodes a Ligand-Gated Ion Channel

The primary structure of the pbo-5 cDNA was determined by reverse transcription and polymerase chain reaction. The pbo-5 cDNA includes an SL1 trans-spliced leader sequence at the 5' end and a total of 9 exons spanning a 7 kb genomic region (FIG. 2). The pbo-5 mutations fall into four categories: (1) nine deletions (2) three nonsense (3) seven missense, and (4) one splice junction mutation (Table 1). The predicted pbo-5 cDNA encodes a 499 amino acid protein (FIG. 3).

BLAST and protein motif queries of PBO-5 suggest that it is a member of the ligand-gated ion channel superfamily. Ligand-gated ion channels are oligomeric receptor complexes containing an integral ion channel that is opened upon ligand binding (Betz, 1990). Ion channels that are gated by acetylcholine, serotonin, γ-aminobutyric acid, and glycine are a superfamily of homologous neurotransmitter receptors, termed the cys-loop superfamily. Although over 100 ligand-gated ion channel subunits have been identified in numerous organisms, each subunit can be assigned to one of the four receptor families based on sequence similarity, and/or functional activity. All ligand-gated ion channel subunits share a common structural and functional homology and have a high degree of amino acid similarity. The subunits are demarcated by a signal peptide, an extracellular amino-terminus that contains consensus ligand binding sites and an invariant disulfide bonded loop (cys-loop), four transmembrane domains (M1-M4), a large cytoplasmic loop between M3-M4, and a short extracellular carboxy terminus (Karlin and Akabas, 1995; Ortells and Lunt, 1995) (FIG. 2). Electron microscopy, electrophysiological and structural data suggest that ligand-gated ion channels are formed from five homologous subunits that are pseudo-symmetrically arranged around a central ion channel, such that the M2 domain lines the ion-channel wall and determines ion selectivity (Betz, 1990; Brejc et al., 2001; Unwin, 1993).

Figure 4:
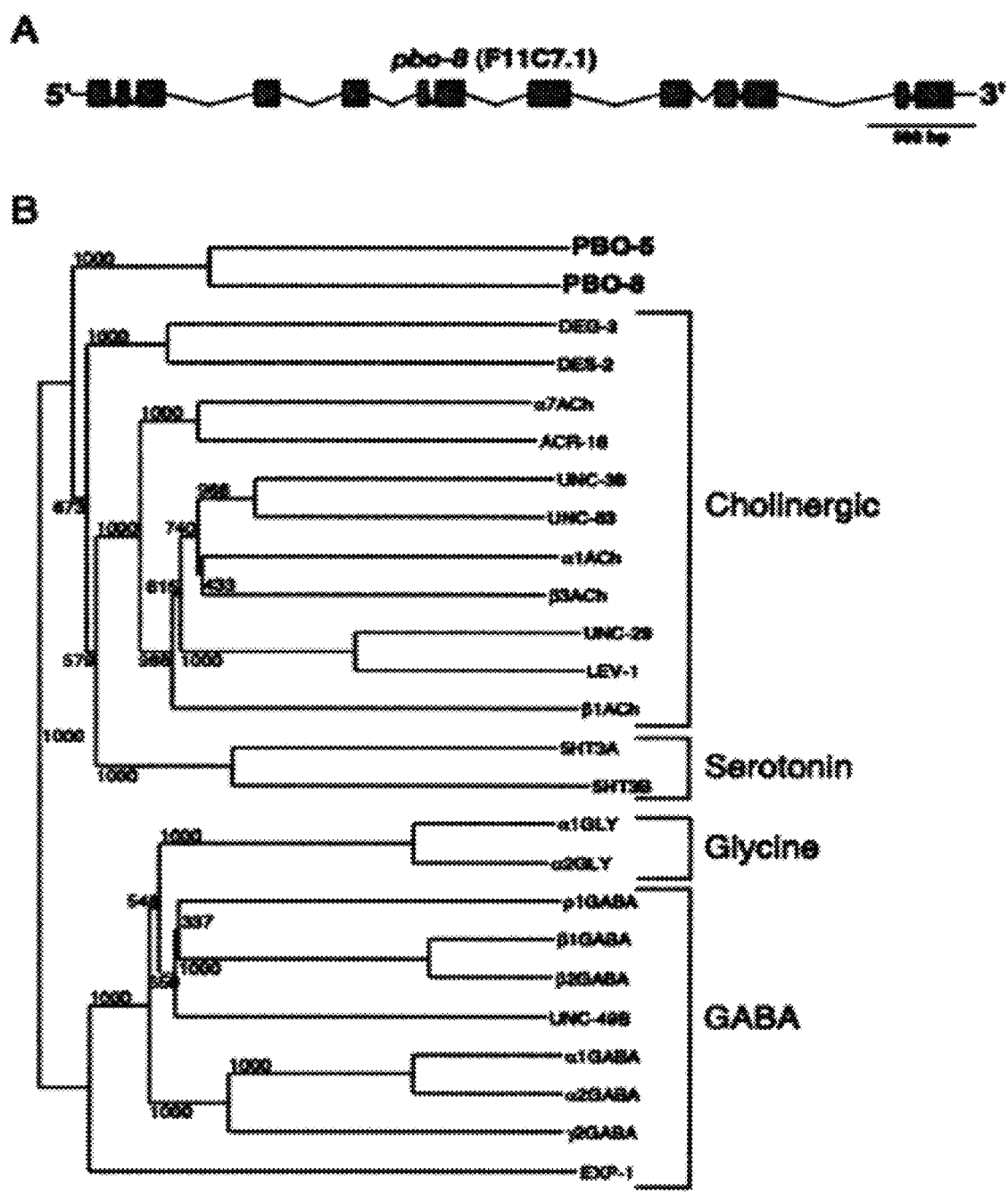
FIG. 4 shows the pbo-8 genomic structure and a phylogenetic tree.

Hydropathy plots and alignment of PBO-5 with various ligand-gated ion channel subunits demonstrates that PBO-5 contains the hallmarks of ligand-gated ion channels (FIG. 3). Additionally, PBO-5 contains many residues that underpin the conserved secondary structure of the cys-loop ligand-gated ion channel superfamily (Brejc et al., 2001). BLAST searches of PBO-5 against human, mouse, *Drosophila*, and *C. elegans* genomes suggest that PBO-5 most closely resembles cholinergic receptors. However, phylogenetic analysis demonstrates that PBO-5, and related orthologs, represents a divergent subunit that cannot be categorized into one of the four families based on sequence similarity (FIG. 4). BLAST searches against the *C. elegans* genome revealed another predicted protein, PBO-8, which contained high sequence identity to PBO-5. For example, accession numbers P12389, O08952 and Q7T2T8. Based on sequence similarity and residues known to be involved with specific ligand sensitivity, the ligand for the PBO-5 receptor was not clearly identifiable from the native sequence. Further, mutants that are defective in GABA, acetylcholine, serotonin, and peptidergic neurotransmission do not exhibit posterior body contraction defects. Therefore, it seemed unlikely that PBO-5 would be activated by known classical neurotransmitters.

pbo-5 is Expressed in the Posterior Body Wall Muscles

Figure 5:
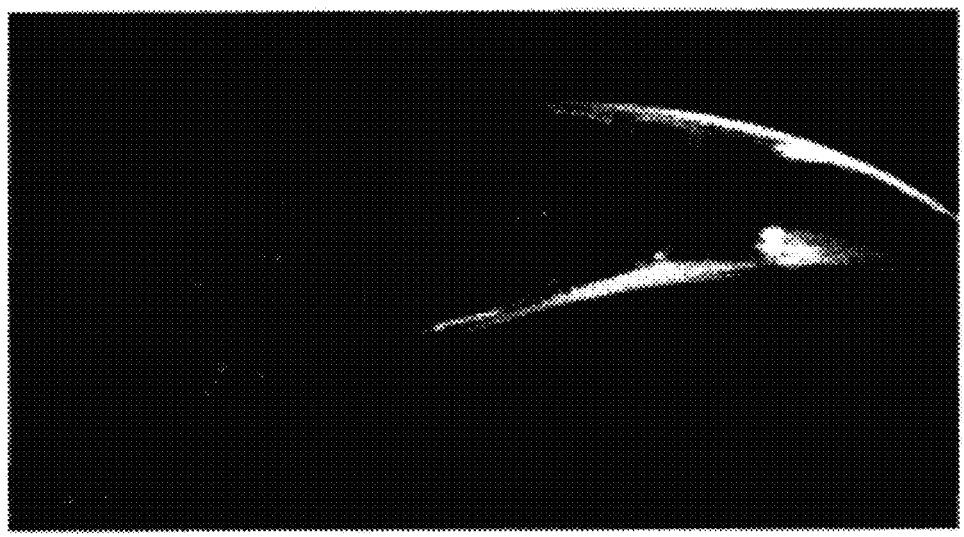
FIG. 5 shows the expression pattern of pbo-5.
Figure 5:
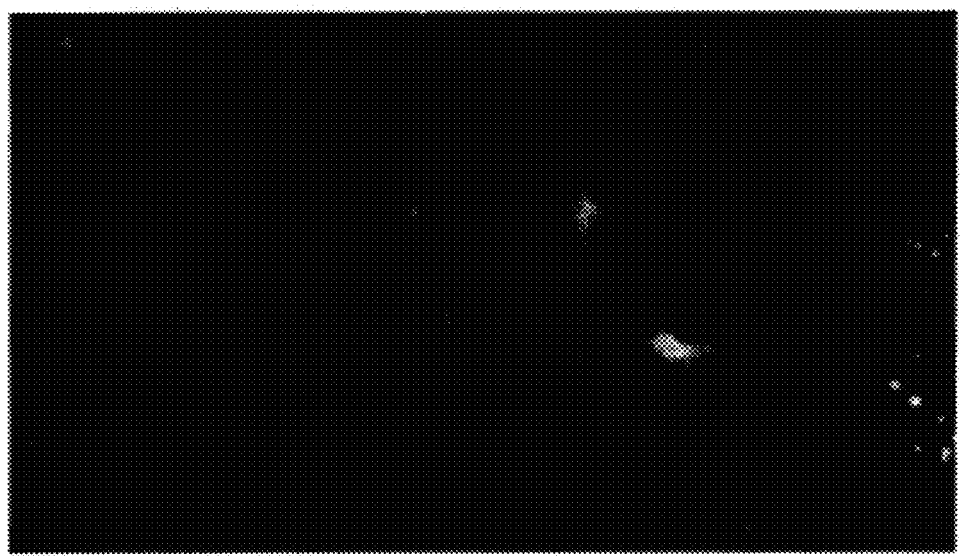
Figure 5:

If PBO-5 is the receptor that mediates posterior body contraction then it should be expressed in the body wall muscles. To determine the cellular expression of pbo-5, a transcriptional pbo-5::gfp fusion gene was constructed that contained 3.8 kb upstream sequence of the translational start codon fused to the GFP open reading frame (Chalfie et al., 1994). Stable chromosomally integrated lines of this construct expressed GFP in the most posterior muscle cells of the tail and in a small number of neurons in the head (FIG. 5). The expression pattern of PBO-5 demonstrates that it is expressed in the appropriate cells to mediate posterior body contraction.

PBO-5 is not Activated by Classical Neurotransmitters

To determine if PBO-5 can form a homo-oligomeric receptor, we injected PBO-5 cRNA in *Xenopus oocytes*. Since sequence information did not confidently predict the ligand that would activate the putative PBO-5 receptor, a candidate approach was undertaken to ascertain the ligand. Two-electrode voltage clamp recordings were used to assay receptor functionality. A host of classical neurotransmitters such as acetylcholine, choline, GABA, glycine and serotonin were applied to PBO-5 injected oocytes, yet all ligands failed to elicit a functional response.

Typically, muscle type acetylcholine receptors require both α and non-α subunits to form functional receptors. The predicted PBO-8 protein is the most closely related to PBO-5 of all predicted cholinergic-like receptors in *C. elegans* (FIG. 4).

PBO-8 Primary Structure and Expression

Figure 6A:
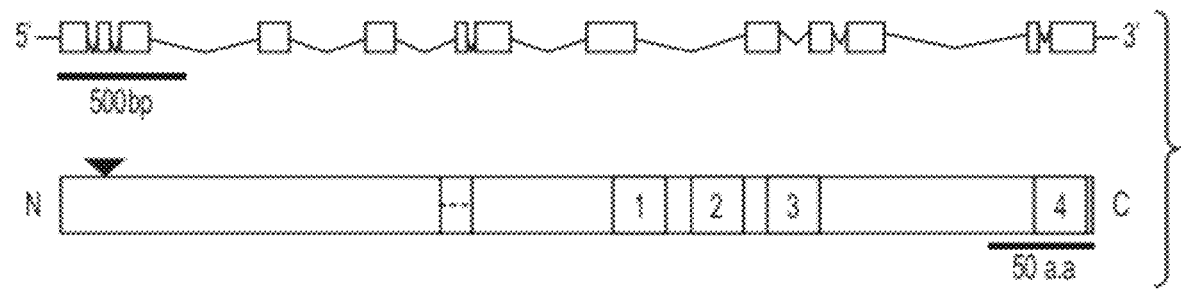
FIG. 6 illustrates the structure and molecular cloning of pbo-8. The top of FIG. 6A represents the exon-intron structure of pbo-8; below, the predicted protein structure. The triangle represents the predicted signal peptide cleavage site, the dotted line represents the disulfide-bond, and the numbers 1-4 represent the four transmembrane domains.
FIG. 6B shows the expression pattern of PBO-8. The left panel is a confocal image of an animal expressing a transcriptional pbo-5::gfp fusion gene. The right panel is a fluorescent image of an animal expressing a transcriptional pbo-8::gfp fusion gene fusion. PBO-8 expression is observed in the most posterior muscle cells, and has overlapping expression with PBO-5, suggesting PBO-8 may oligomerize with PBO-5 to form a functional receptor.
Figure 6B:
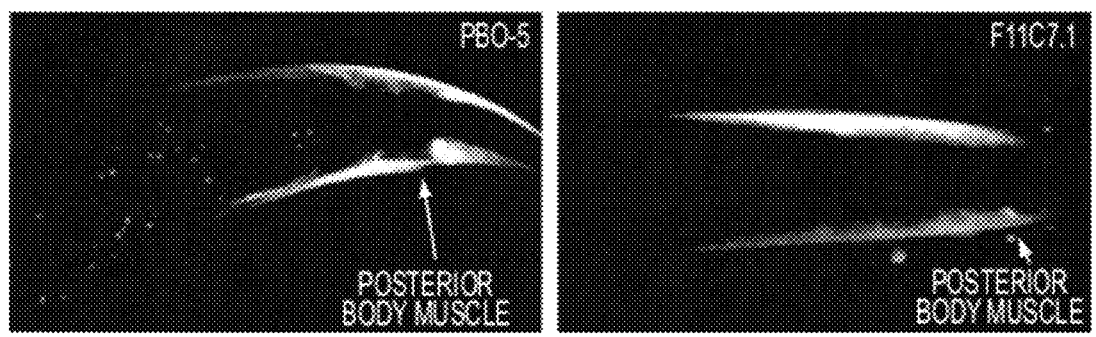

The pbo-8 predicted open reading frame encodes a protein that is homologous to ligand-gated ion channels (FIG. 3). Significantly, the PBO-8 protein most closely resembles PBO-5 (FIG. 4). To determine the primary structure of PBO-8 RT-PCR was performed and full-length cDNA clones isolated. The PBO-8 full-length cDNA consists of 13 exons that span 4.1 kb of genomic DNA (FIG. 6A). The PBO-8 cDNA encodes a 423 amino acid protein (FIG. 6A). We performed protein alignments with PBO-8 and PBO-5 revealing they share 35% identity. With the exception of one conservative amino acid change, the residues in the M2 domain are identical (FIG. 3). If PBO-8 oligomerizes with PBO-5 to form a functional receptor, then PBO-8 should have overlapping expression with PBO-5. To address the expression pattern of PBO-8, a transcriptional fusion containing 4 kb of upstream promoter sequence fused to GFP was constructed. GFP expression was observed in the most posterior body wall muscles in the tail, identical to PBO-5 expression (FIG. 6B). These data suggest that PBO-8 may oligomerize with PBO-5 to form a functional receptor.

PBO-5/PBO-8 Forms a If-Gated Ion Channel

To determine if PBO-5 and PBO-8 can co-assemble to form a functional receptor, we injected PBO-5 and PBO-8 cRNA into *Xenopus oocytes*. Agonists which function at other ligand-gated ion channels (such as, ACh, GABA, glycine, 5-HT, glutamate, and choline) lacked the ability to activate PBO-5 homomers, PBO-8 homomers or PBO-5/PBO-8 heteromers. Activation of receptors was not unexpected because genetic evidence demonstrates acetylcholine, GABA, glutamate and serotonin are not required for posterior body contraction. To determine the possible signal that mediates posterior body contraction we examined the pbo-4 gene.

The predicted pbo-4 gene encodes a protein related to $Na^+/H^+$ exchangers. PBO-4 is expressed in the posterior intestine and is required for posterior body contraction. $Na^+/H^+$ exchangers mediate the exchange of one $Na^+$ into the cell for one $H^+$ out of the cell. The expression of PBO-4 in the posterior intestine parallels the expression pattern of PBO-5 and PBO-8 in the posterior body wall muscles. These data suggest that PBO-4 mediates the secretion of $H^+$ from the intestine, into the pseudocoelomic space, adjacent to PBO-5/PBO-8 posterior muscle expression. Therefore, without wishing to be bound by theory, we hypothesized that $H^+$ ions may activate or may be required for co-activation of PBO-5/PBO-8 receptors.

Figure 7:
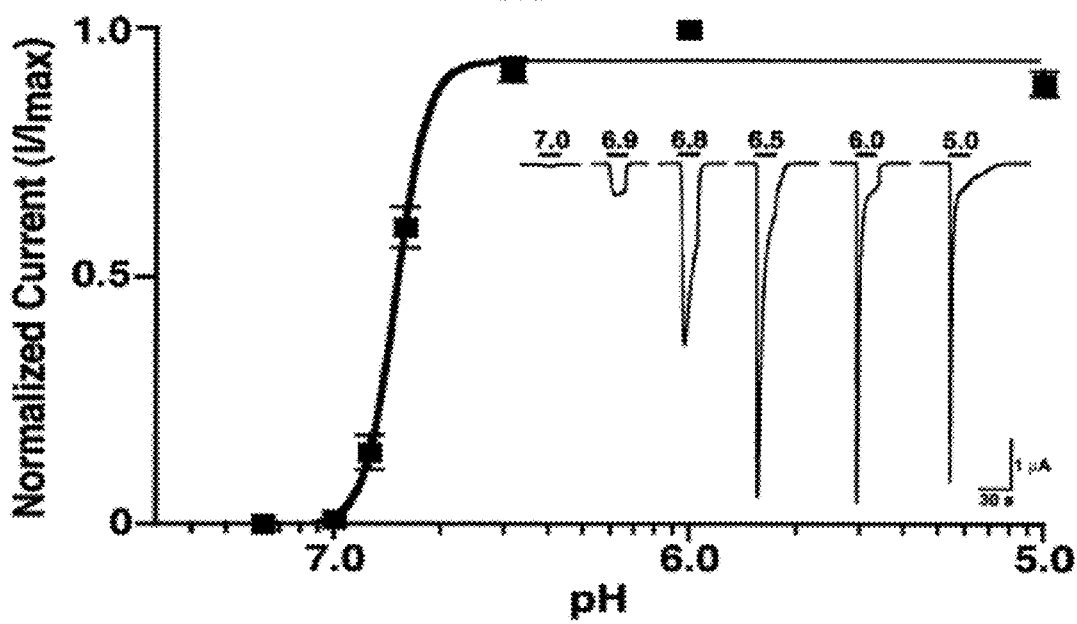
FIG. 7 shows a pH dose-response curve for PBO-5/PBO-8, which form a heteromultimeric H$^+$-gated ion channel. PBO-5/PBO-8 expressing oocytes were voltage-clamped at −60 mV and a series of test pH applications (7.2-5.0) were bath applied for 5 seconds. Each point represents the mean current value normalized to the maximum and minimum values. A pH$_{50}$=6.83±0.01 and Hill coefficient of 9+0.66 were determined for PBO-5/PBO-8 receptors (n=18). Error bars represent s.e.m. Inset, representative traces of PBO-5/PBO-8 dose-response experiments.

To determine if $H^+$ ions are sufficient to activate PBO-5/PBO-8 receptors, we applied test pulses of varying pH to PBO-5/PBO-8 expressing cells. Test pulses of pH 6.8 evoked robust inward currents, indicating that $H^+$ ions are sufficient to activate recombinant receptors (FIG. 7, inset). To demonstrate that current responses evoked by changes in pH were not due to endogenous channels or transporters, we applied maximal test pulses of pH 5.0 to water injected and uninjected oocytes. Only oocytes injected with PBO-5/PBO-8 cRNA exhibited $H^+$-gated responses. To determine if PBO-5 and PBO-8 can form functional homomeric $H^+$-gated ion channels, we injected each subunit alone into oocytes. Injection of PBO-5 or PBO-8 cRNA into oocytes, resulted in little or no functional expression compared to oocytes co-injected with PBO-5 and PBO-8 cRNA. These data suggest that the PBO-5/PBO-8 heteromultimerization is required for efficient functional receptor expression in vitro.

$H^+$ ions have been demonstrated to modulate classical synaptic transmission. For example, acidic changes in pH inhibit acetylcholine receptor function, where alkaline environments enhance receptor function (Palma et al., 1991; Pasternack et al., 1992). To determine whether or not classical neurotransmitters co-activate PBO-5/PBO-8 receptors, we applied pH 6.8 with and without 1 mM ligand. Application of pH 6.8 plus acetylcholine, choline or GABA was not significantly different from pH 6.8 only application (data not shown). Taken together, these data suggest that $H^+$ ions alone are sufficient to fully activate PBO-5/PBO-8 receptors.

To determine the pH50 (half-maximal activation) of PBO-5/PBO-8 heteromultimers, we first identified the pH range at which the recombinant receptors were activated. We determined that the PHIO (10% maximal activation) was approximately pH 7.0. We set our perfusion buffer at pH 7.4 for all experiments, where no activation of recombinant receptors was observed. A $pH_{50}=6.83\pm0.01$ was determined by applying decreasing pH test pulses (pH 7.0-5.0). A steep Hill coefficient of $9\pm0.66$ was determined, demonstrating PBO-5/PBO-8 receptors exhibit significant $H^+$ binding cooperativity (FIG. 7).

PBO-5/PBO-8 Ion-Selectivity

Figure 8:
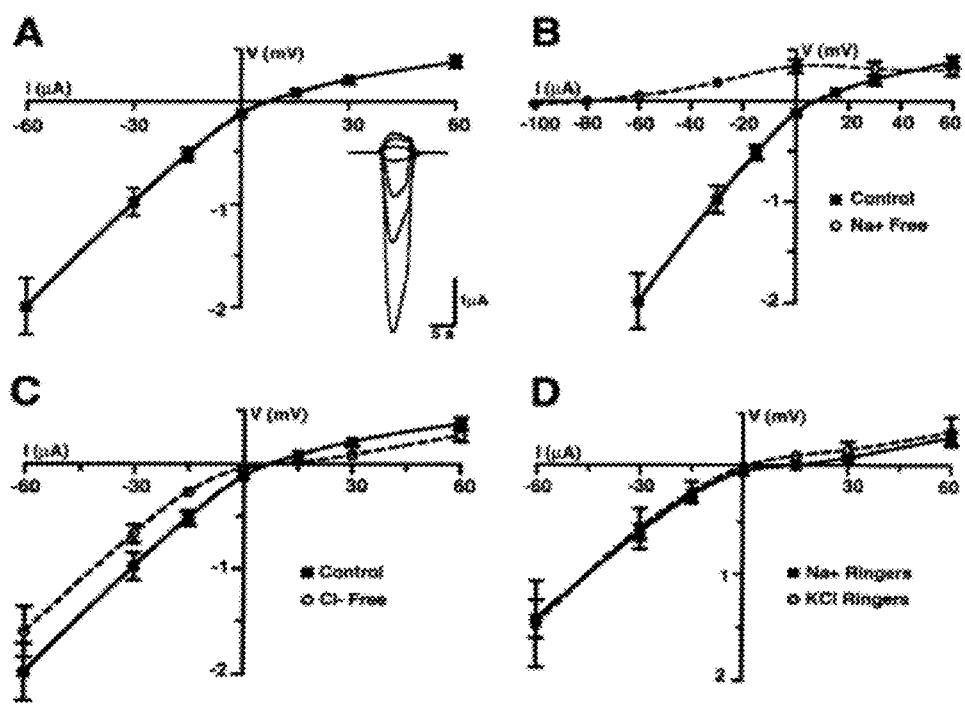
FIG. 8 shows PBO-5/PBO-8 ion selectivity.

Current-voltage (I-V) analysis was used to characterize the ionic conductance underlying PBO-5/PBO-8 responses. The H-gated current had a reversal potential of $10.18\pm0.80$ mV in Ringer's solution (FIG. 8A). The I-V relationship demonstrates that PBO-5/PBO-8 exhibits inward rectification (FIG. 8A, inset). The positive reversal potential suggests that PBO-5/PBO-8 encodes a cation-selective ion channel. To determine if $Na^+$ underlies PBO-5/PBO-8 $H^+$-evoked responses, we replaced $Na^+$ with the large cation N-methyl D-glucamine In $Na^+$-free solution, the inward current was eliminated and the reversal potential was $-82.90\pm8.13$ mV (FIG. 8B). Furthermore, to demonstrate anions such as $Cl^-$ do not flow through PBO-5/PBO-8 channels, we replaced extracellular $Cl^-$ with the impermeable anion gluconate. In $C^-$ free solution, the inward current remained with no significant shift in reversal potential ($\Delta E_{rev}=0.25$ mV, $P>0.05$, two-way ANOVA), compared to control (FIG. 8C). This demonstrates $Na^+$ is the primary charge carrier through PBO-5/PBO-8 channels.

To determine the cation-selectivity of the PBO-5/PBO-8 ion channel, we substituted extracellular $Na^+$ with equivalent $K^+$. In $K^+$ Ringer's solution, I-V relationships were not significantly different ($P>0.05$ two-way ANOVA) compared to $Na^+$ Ringers control (FIG. 8D). Additionally, strong inward rectification was present in I-Vs determined in $K^+$ Ringers, demonstrating rectification was not due to ion-selectivity. Taken together, these data demonstrate PBO-5/PBO-8 encodes a non-selective inwardly rectifying cation channel.

Next, $Ca^{2+}$ permeability of the PBO-5/PBO-8 ion channels was assayed. The I-V relationships under three $Ca^{2+}$ concentrations: 1 mm control, 3 mM, and 10 mM, were determined Increasing calcium to 10 mM resulted in a positive shift in reversal potential from control (FIG. 9A). To better resolve calcium permeability, NaCl was replaced with NMDG in the extracellular solution, making $Ca^{2+}$ the only relevant extracellular ion. Increasing $Ca^{2+}$ in this solution revealed that PBO-5/PBO-8 channels are calcium permeable. Increasing $Ca^{2+}$ 10 fold caused a +50 mV shift in reversal potential compared to control (FIG. 9B).

Figure 9:
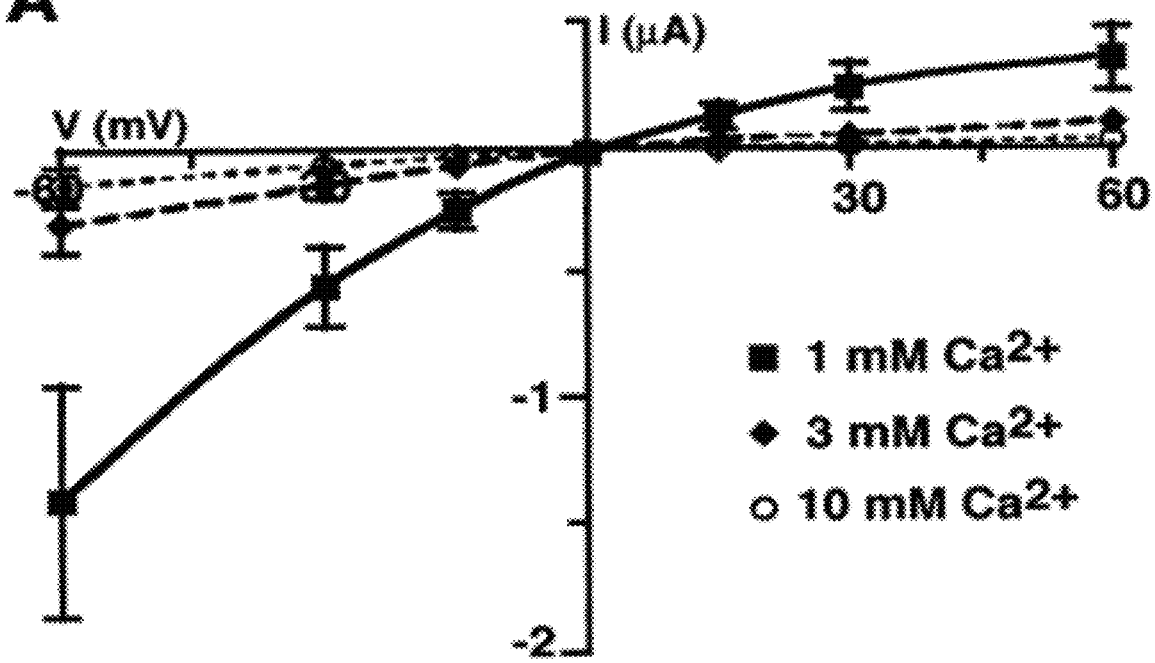
FIG. 9 shows calcium permeability.
Figure 9:
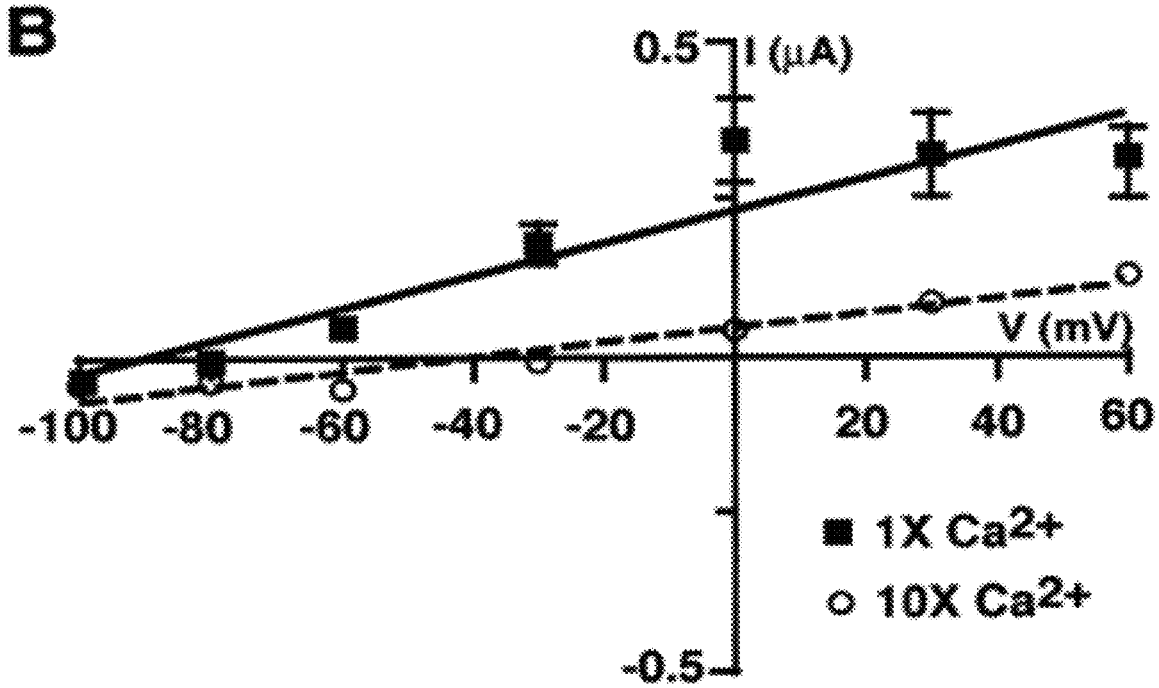

Interestingly, $H^+$-evoked inward currents were significantly reduced as extracellular $Ca^{2+}$ was increased (FIG. 9). Specifically, a control pulse of pH 6.8 with 1.0 mM $Ca^{2+}$ evoked a large response, and an equivalent test pulse of pH 6.8 with 10.0 mM $Ca^{2+}$ evoked a much smaller response. This suggests that, while $Ca^{2+}$ is permeable, high amounts of $Ca^{2+}$ inhibit gating of PBO-5/PBO-8 channels.

Figure 10:
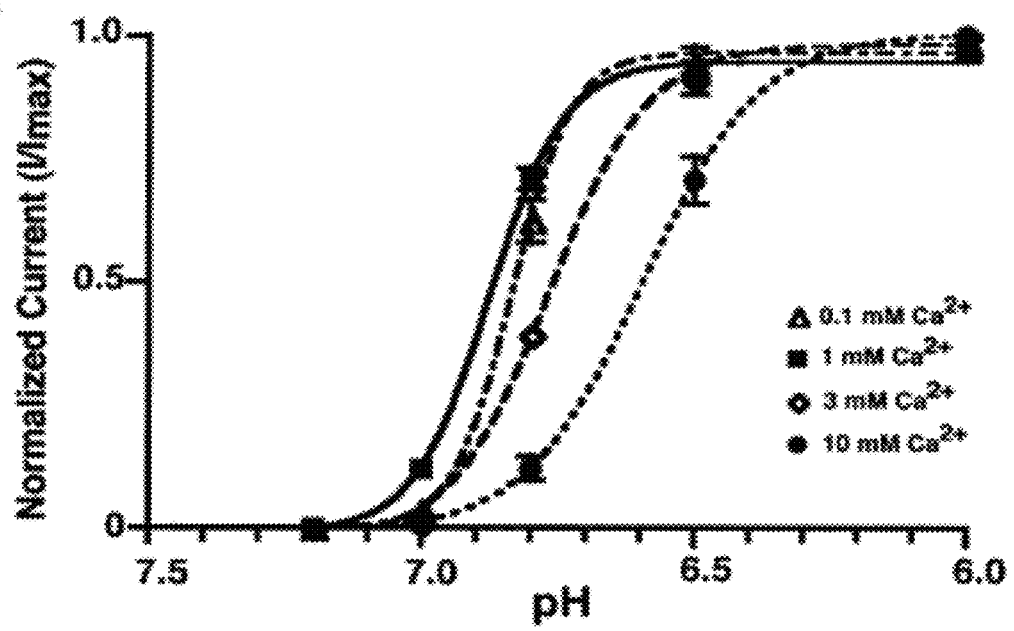
FIG. 10 shows that $Ca^{2+}$ and $H^+$ compete at the PBO-5/PBO-8 activation site.
Figure 10:
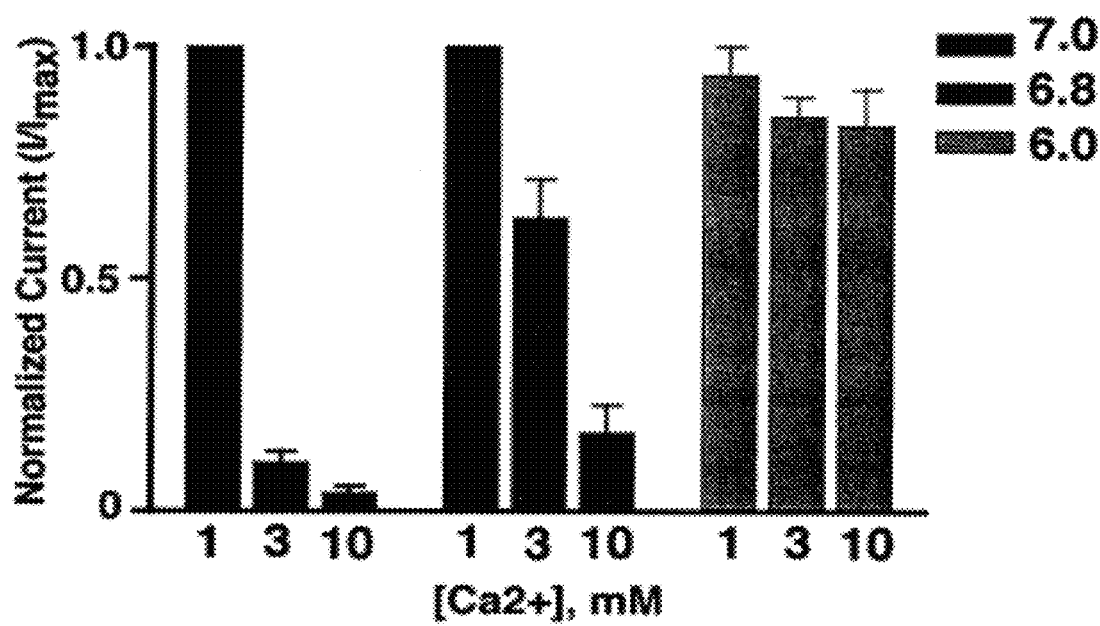

To further investigate the $Ca^{2+}$ inhibition of PBO-5/PBO-8 receptors, dose response experiments were performed under different extracellular $Ca^{2+}$ conditions (0.1, 1, 3, 10 mM). PBO-5/PBO-8 receptors under 1 mM $Ca^{2+}$ control conditions exhibited a $pH_{50}=6.88$ and a Hill coefficient of 6 (FIG. 10A). As $Ca^{2+}$ was increased to 10 mM a right shift in the activation curve of PBO-5/PBO-8 was observed. Specifically, a significantly different $pH_{50}=6.59$ and a Hill coefficient of 4 was determined under 10 mM $Ca^{2+}$ test conditions (FIG. 10A). These data demonstrate that as extracellular $Ca^{2+}$ is increased, $H^+$ sensitivity and cooperativity decrease.

Next, to determine if increasing extracellular $Ca^{2+}$ caused an inhibition of maximal PBO-5/PBO-8 activation, $Ca^{2+}$ conditions at three different pH ranges (7.0, 6.8, and 6.0) were applied. H-evoked responses were significantly reduced, compared to 1 mM $Ca^{2+}$ control, at pH 7.0 and 6.8 as $Ca^{2+}$ was increased to 3 mM and 10 mM (FIG. 10B). However, at pH 6.0, increasing extracellular $Ca^{2+}$ had no effect on maximal activation of PBO-5/PBO-8 (FIG. 10B). These data suggest that $Ca^{2+}$ acts as a competitive antagonist at PBO-5/PBO-8 receptors. We are further examining the mechanism of $Ca^{2+}$ antagonism to PBO-5/PBO-8 receptors.

Discussion

It is demonstrated that pbo-5 encodes a novel ligand-gated ion channel subunit required to initiate the posterior body contraction of the defecation cycle. Loss of pbo-5 activity specifically eliminates the posterior body contraction, while gain-of function alleles result in hypercontraction of the posterior body muscles. PBO-5 is expressed in the most posterior muscle cells of the tail, suggesting it is properly localized to mediate the posterior body contraction. Finally, it is demonstrated that PBO-5 heteromultimerizes with PBO-8 to form a novel $H^+$-gated ion channel when expressed in Xenopus oocytes. The channel encoded by PBO-5/PBO-8 is a nonselective inward rectifying cation channel. The molecular identification and functional characterization of the PBO-5 and PBO-8 receptor subunits defines a novel group of the cys-loop ligand-gated ion channel superfamily. Furthermore, the functional characterization of $H^+$-sensitivity demonstrates that the PBO-5/PBO-8 signaling pathway defines a novel mechanism of cellular communication.

$H^+$ Dependence of PBO-5/PBO-8

The overlapping cellular expression of PBO-5 and PBO-8 in the most posterior body muscles of that tail, coupled with the fact that functional receptor expression is only observed when both PBO-5 and PBO-8 are coinjected into oocytes, strongly suggests the PBO-5/PBO-8 represents the native receptor that mediates posterior body contraction. We have demonstrated that $H^+$ ions are sufficient to activate PBO-5/PBO-8 receptors.

The defecation cycle in a wild-type animal occurs every 50 seconds with little variability and the first muscle contraction to occur is the posterior body contraction. It has been demonstrated that periodic calcium release in the intestine correlates with the onset of the posterior body contraction (Dal Santo et al., 1999). The itr-1 gene which encodes an inositol triphosphate ($IP_3$) receptor is required in the intestine for proper defecation cycle timing (Dal Santo et al., 1999). Hypomorphic itr-1 alleles exhibit long or no defecation cycle cycles (>50 seconds), while overexpression of itr-1 results in short defecation cycle times (<50 seconds). Furthermore, calcium imaging of itr-1 hypomorphic alleles that have no defecation cycles (i.e., no posterior body contraction) fail to exhibit calcium oscillations (Dal Santo et al., 1999). Taken together, these data suggest that $IP_3$ receptor activity in the intestine is required for the signaling of each muscle contraction in the defecation cycle.

The posterior body contraction is the initial contraction in the defecation motor program, and does not rely on neuronal input. The PBO-5/PBO-8 receptor is gated by $H^+$ ions, and PBO-5 is required for posterior body contraction. It has been demonstrated that $IP_3$ receptor (itr-1) mediated calcium signaling in the intestine is required for the activation of the posterior body contraction (Dal Santo et al., 1999). However, the nature of the signal was unknown as mutants with defects in classical neurotransmission have normal posterior body contraction.

The pbo-4 gene encodes a protein that has similarity to $Na^+/H^+$ exchangers (NHEs). pbo-4 mutants are phenotypically identical to pbo-5 mutants, and the pbo-4; pbo-5 double mutant is identical to both single mutants. This suggests that pbo-4 and pbo-5 are in the same signaling pathway that mediates posterior body contraction.

Furthermore, the expression pattern of pbo-4 is restricted to the posterior intestine, adjacent to the muscle expression of PBO-5 and PBO-8. $Na^+/H^+$ exchangers have been implicated in a number of processes including intracellular pH and cell volume regulation, and in reabsorption of NaCl across epithelial cells (Counillon and Pouyssegur, 2000; Orlowski and Grinstein, 1997). Plasma membrane NHEs mediate the electroneutral exchange of $Na^+$ ions into the cell for $H^+$ ions out, thereby acidifying the extracellular environment while increasing intracellular pH. Mammalian NHEs are regulated by a number of factors including phosphorylation, calcium, and by interactions with accessory proteins (Orlowski and Grinstein, 1997). For example, mammalian NHE1 is sensitive to increases in cytosolic $Ca^{2+}$, due to a high-affinity calmodulin binding site present on the C-terminal tail of the protein (Bertrand et al., 1994). Deletion of this binding site causes NHE1 to be constitutively active (Wakabayashi et al., 1994; Wakabayashi et al., 1997). Therefore, under normal conditions (low $Ca^{2+}$), the calmodulin-binding site is unoccupied and exerts an inhibitory effect. An intracellular rise in $Ca^{2+}$ stimulates $Ca^{2+}$/calmodulin binding to NHE1, thereby releasing inhibition, and activating $Na^+/H^+$ exchange. Analysis of the C-terminal tail of the PBO-4 protein predicts a putative calmodulin binding site as well as a consensus phosphorylation site for CaMKII.

The structural analysis and expression of pbo-4 in the intestine predicts that PBO-4 mediates the exchange of $Na^+$ ions into the intestine for $H^+$ ions out of the intestine into the pseudocoelomic space. $H^+$ binding has been demonstrated herein to be sufficient to activate PBO-5/PBO-8 receptors. Therefore, without wishing to be bound by theory, it is believed that the $H^+$ signal arises from the intestine and $H^+$ transport is mediated by PBO-4.

It has been demonstrated that $IP_3$ receptor mediated release of calcium from the intestine correlates with the onset of the posterior body contraction and is required. Therefore, it is believed that a necessary feature of the posterior body contraction signaling mechanism is that it be modulated by calcium. The pbo-4 gene, expressed in the posterior intestine, encodes a $Na^+/H^+$ exchanger with a predicted $Ca^{2+}$/calmodulin binding domain. It has now been demonstrated that $H^+$ ions are sufficient to activate PBO-5/PBO-8 receptors (e.g., using Xenopus oocytes (in vitro)) that are localized to the posterior body muscles.

Figure 11:
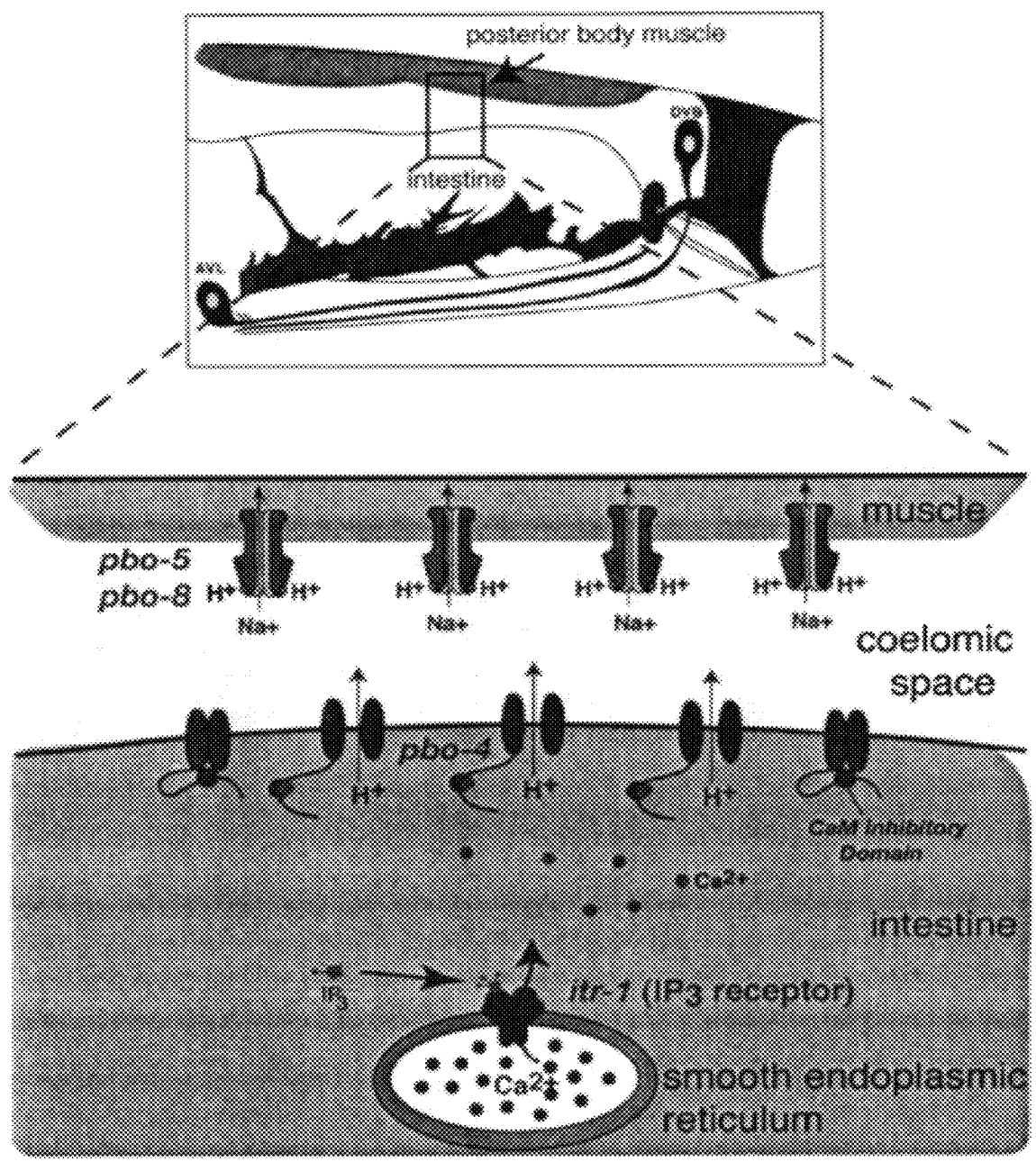
FIG. 11 illustrates an exemplary embodiment for posterior body contraction in C. elegans. Every 50 seconds, a calcium spike occurs in the intestine the correlates with the initiation of the posterior body contraction. First, $IP_3$ receptors localized to the smooth endoplasmic reticulum in the intestine are activated every 50 seconds. Activation results in the intracellular rise of $Ca^{2+}$ in the intestine. Second, $Ca^{2+}$ binds to the C-terminal calmodulin-binding domain of PBO-4, thereby activating $H^+$ transport activity. Third, PBO-4 transports $H^+$ ions out of the intestine acidifying the pseudocoelomic space. Fourth, $H^+$ ions bind and activate the PBO-5/PBO-8 receptors expressed in posterior body wall muscle, thereby allowing $Na^+$ influx into the cell causing a depolarization and subsequent muscle contraction.
Figure 12A:
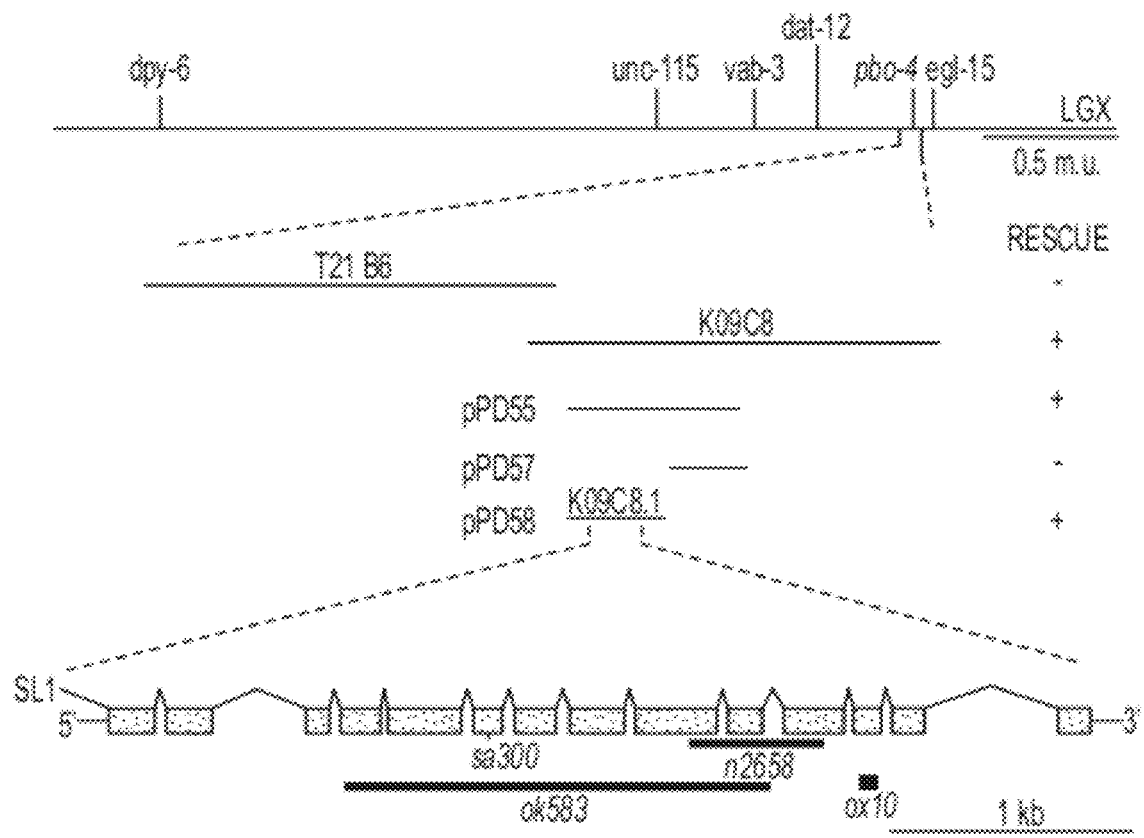
FIG. 12(A) illustrates the pbo-4 locus, which maps between daf-12 and egl-15 on the X chromosome. This region contains the cosmids T21B6 and K09C8. Rescue of the posterior body contraction defect by cosmid or subclone is indicated. Below this is an exon-intron structure of pbo-4. Mutations are indicated, black bars denote the extent of deletion alleles within the locus.
Figure 12B:
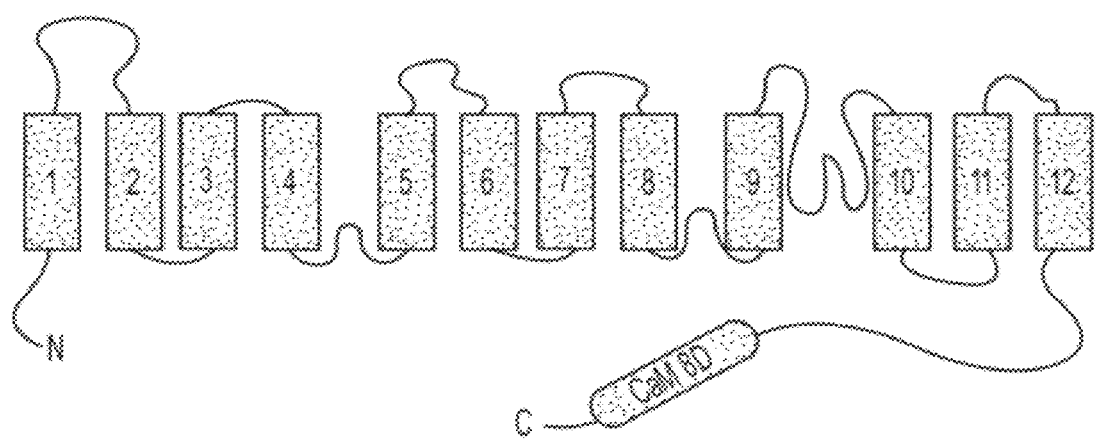
FIG. 12(B) illustrates the predicted PBO-4 protein domains. The predicted protein consists of a signal peptide, 12 transmembrane domain, a re-entrant loop between transmembrane domains 9 and 10 and an intracellular carboxy-terminal tail that contains a predicted calmodulin binding site.

Without wishing to be bound by theory, from this data it is proposed that for posterior body contraction: 1) $IP_3$ receptors localized to the smooth endoplasmic reticulum in the intestine are activated every 50 seconds. Activation results in the intracellular rise of $Ca^{2+}$ in the intestine; 2) $Ca^{2+}$ binds to the C-terminal calmodulin-binding domain of PBO-4, thereby activating $H^+$ transport activity; 3) PBO-4 transports $H^+$ ions out of the intestine acidifying the pseudocoelomic space; and 4) $H^+$ ions bind and activate the PBO-5/PBO-8 receptors expressed in posterior body wall muscle, thereby allowing $Na^+$ influx into the cell causing a depolarization and subsequent muscle contraction (FIG. 11).

This simple model can account for the non-neuronal nature of the posterior body contraction, and involves strict calcium regulation. The present invention demonstrates that PBO-5/PBO-8 receptors are exquisitely sensitive to changes in extracellular pH, as determined in heterologous cells ($pH_{50}$=6.83±0.01). The sensitivity of PBO-5/PBO-8 receptors suggests minor acidification of the pseudocoelomic space is required to activate the posterior body contraction. The pseudocoelomic space separates the intestine from the muscle, and is relatively small as observed in electron micrographs. Thus, the acidification of the pseudocoelomic space at the posterior end of the animal to a pH ~6.8 is not physiologically unreasonable. In vivo recording from the posterior body wall muscles is preformed to recapitulate the in vitro findings.

PBO-5/PBO-8 is a Novel Cys-Loop Ligand-Gated Ion Channel

The PBO-5 and PBO-8 subunits display the structural motifs common to the superfamily of cys-loop ligand-gated ion channels. However, the distinctive sequence and functional activity prevent classification within any of the four established receptor families. Motor behaviors, such as muscle contraction, are typically controlled via fast synaptic transmission between a motor neuron and muscle cell. The present invention demonstrates that $H^+$ ions alone are sufficient to activate recombinant receptors and that co-application of other classical neurotransmitters has little effect on activation. Furthermore, the functional characterization of the receptor and proposed model of excitation provide a unique form of fast non-synaptic communication. Protons have been demonstrated to be modulatory at "cys-loop" ligand-gated ion channels; however, this is the first evidence that protons can directly activate this receptor subclass. Therefore, the present invention demonstrates that $H^+$ fulfills the criteria of a fast transmitter in *C. elegans*.

In one exemplary embodiment mammalian paralogs and/or orthologs are identified, for example by BLAST searches using PBO-5 and PBO-8 sequences (e.g. SEQ ID NOS: 6 and 7), and one or more of the paralogs and/or orthologs is confirmed to be a component of a $H^+$-gated ion channel. In particular, there are a number of predicted cholinergic-like proteins to which PBO-5 and PBO-8 share identity. Changes in extracellular pH have been demonstrated to regulate ion channel function, hi most cases, $H^+$ ions modulate classical neurotransmission by inhibiting or exciting various classical ligand-gated ion channels. While it has been demonstrated that $H^+$ signaling is a major pathway for pain sensation through the acid-sensing ion channels (ASIC), direct $H^+$ signaling has never been associated with cys-loop ligand-gated ion channels (Waldmann et al., 1997; Waldmann et al., 1999).

Recently, a novel $Zn^{2+}$ activated ligand-gated ion channel (ZAC) has been cloned and characterized in humans (Davies et al., 2003). The ZAC channel represents a distinct class of cys-loop ligand-gated ion channels that is not activated by classical neurotransmitters. Interestingly, the ZAC subunit has been retained in some mammals (human and dog), but has been lost by others (mouse and rat), demonstrating specific cell signaling mechanisms may vary across species. Therefore, an exemplary embodiment of the invention provides a method for the identification and characterization of the $H^+$ gated PBO-5/PBO-8 receptor in other species.

In an exemplary embodiment, the pharmacology of the PBO-5/PBO-8 receptor is determined, in another exemplary embodiment modulation of PBO-4 by $Ca^{2+}$ is determined In yet another exemplary embodiment, isolation of PBO-8 mutants is performed and the mutant phenotype assayed relative to PBO-5 and/or PBO-4. Optionally, genetic analysis is conducted to determine if PBO-8 is in the same genetic pathway as PBO-5 and/or PBO-4.

To determine if $H^+$ ions are required to initiate a posterior body contraction endogenous acidification of the pseudocoelomic space is blocked. For example, 100 mM Bis-Tris Propane buffered saline (pH 7.2) is injected into the pseudocoelomic space of an animal and defecation cycles postinjection observed. It is believed that animals that have had buffered saline injected into the pseudocoelomic space will fail to initiate a posterior body contraction while all other steps of the defecation cycle will be normal. The injected animals should phenocopy both pbo-4 and pbo-5 mutants.

Alternatively, a caged buffer is used to assay the requirement for $H^+$ activation of PBO-5/PBO-8 receptors in vivo. For example, animals are injected with a caged buffer (Molecular Probes) and the buffer uncaged, by flash photolysis, as a posterior body contraction is about to occur. An advantage of the latter scheme is that an animal can be injected first and then observed for a number of cycles to determine if it retains normal defecation cycles, and in particular posterior body contractions. After quantification of a number of defecation cycles, the buffer is uncaged and the animal observed for a specific loss of posterior body contraction. Li addition, the inverse experiment, where caged protons are injected, may be conducted to elicit an out of phase posterior body contraction by uncaging the protons during the intercycle.

Functional Analysis of Dominant pbo-5 Alleles

Several of the pbo-5 mutations provide particularly interesting insights into the structure and function of the PBO-5 protein. Loss-of-function mutations cause an absence of posterior body contraction, while gain-of-function mutations cause hypercontraction. Two dominant alleles (n2331 and ox7) result in the same mutation within the M2 domain of the ion channel. Specifically, residue 316 is mutated from leucine to phenylalanine (L316F). The M2 domain lines the ion channel wall, and residues in and around M2 affect ion selectivity and receptor desensitization (Leonard et al., 1988). An adjacent residue is altered in the M2 domain of the cholinergic DEG-3 gain-of-function mutant, and causes cell death (Treinin and Chalfie, 1995). It was proposed that prolonged opening and increased ion flow through DEG-3 ion channels underlies the degeneration. Similarly, dominant gain-of-function mutations within the M2 domain of acetylcholine receptors leads to increased ion flow through slower channel closure (Engel et al., 1996). Therefore, it is believed that the cramp phenotype observed in the dominant alleles is due to a channel that has slower inactivation.

To determine if pbo-5 (n2331dm) encodes a slowly inactivating receptor, cDNAs that carry the mutation are isolated and pbo-5 (n2331dm) cRNA is coexpressed with wild-20 type PBO-8, and receptor function is assayed. It is believed that pbo-5 (n2331dm) will result in a response to acidic pH application that is prolonged and enduring, rather than desensitizing as in the wild-type.

PBO-5/PBO-8 Pharmacology

PBO-5/PBO-8 forms a heteromultimeric $H^+$-gated cation channel and extracellular $Ca^{2+}$ concentration affects PBO-5/PBO-8 pH sensitivity. The PBO-5/PBO-8 receptor subunits are structurally related to the ligand-gated ion channel superfamily, and sequence analysis and functional activity place the PBO-5/PBO-8 receptor into a previously unknown family (FIG. 4). hi an exemplary embodiment, $H^+$-gated cation channel receptors are identified and assayed for sensitivity to known ligand-gated ion channel agonists and antagonist. In addition, $H^+$-gated cation channel receptors are identified in a subject, for example, a mammalian or vertebrate subject, such as a human, and assayed for functions described herein. Such mammalian, or vertebrate, receptors are assayed for drug interactions with have agonist, antagonist or blocking activity.

For example, it was observed during electrophysiological investigation of PBO-5/PBO-8 that the buffer HEPES (N-2-hydroxyethylpiperazine-N'-2-ethanesulfonic acid) in our extracellular solution produced a very rapid rundown of the $H^+$-evoked current that could not be explained by poor oocyte health. An initial pulse of pH 6.8 HEPES buffered solution gave a robust inward current. However, subsequent application of pH 6.8 HEPES caused a marked reduction in inward current. Eventually, PBO-/PBO-8 receptors could be run-down to zero current with repeated pH 6.8 applications that was not reversible with time or supramaximal pH 5.0 application. Initially an extracellular ion replacement was conducted, since a divalent ion such as $Ca^{2+}$ could impart the current block. However, $Ca^{2+}$ reduced solutions still exhibited use-dependent block, therefore, the buffer containing HEPES was substituted with Bis-Tris Propane (1,3-Bis[tris(hydroxymethyl)methylamino) propane or MES (2-(N-Morpholino)-ethanesulfonic acid.

When HEPES was replaced with either Bis-Tris Propane or MES, repeated acidic pH test pulses did not cause current run-down. Therefore, HEPES was shown to be inhibitory to the receptor. Furthermore, HEPES was demonstrated to be the relevant blocking molecule by applying pH 6.8 pulses of HEPES buffered solution until the evoked current was run down to zero. Following pulsed run down, a pH 6.8 pulse of Bis-Tris propane was applied to the run down receptors. Application of pH 6.8 Bis-Tris Propane or MES buffered solutions to rundown receptors, evoked a robust inward current. Specifically, a current equal to or greater than the initial pH 6.8 HEPES response was obtained.

How can HEPES be inhibiting the channel? Recently, the structure of an acetylcholine binding protein (AChBP) that is homologous to the N-terminus of acetylcholine receptors has been resolved (Brejc et al, 2001). The structure of this protein agrees with the predicted N-terminal structure of ligand-gated ion channels. Importantly, it was determined that the ligand binding sites are located at each of the five subunit interfaces, which are located in the extracellular N-terminal part of the protein. Interestingly, the resolved crystal structure contained a HEPES molecule present in each ligand-binding site. In the structure it was determined that HEPES made no specific hydrogen bond with the protein, but its quaternary ammonium group stacked onto Trp143 making cation-π interactions (Brejc et al., 2001). These data suggest that the HEPES molecule may be occluding the $H^+$-binding site of PBO-5/PBO-8 receptors. In an exemplary embodiment, mutations are made in and around the presumptive ligand-binding pocket and assayed for abolishment of HEPES inhibition.

As the PBO-5/8 receptor is exclusively activated by $H^+$, it was next determined if PBO-5/8 gating could be blocked with amiloride. Amiloride is a commonly used pharmacological agent used to block acid sensing ion channels (ASIC). Application of 1 mm amiloride to PBO-5/8 expressing cells did not result current block, demonstrating the H-gating mechanism of PBO-5/8 receptors is different from the ASIC channels. Furthermore, common cholinergic antagonist such as d-tubocurare were applied to PBO-5/8 expressing cells, but all attempts to pharmacologically block PBO-5/8 responses failed. These data suggest the gating mechanism of PBO-5/8 receptors is quite different from both cholinergic and ASIC receptors.

In an exemplary embodiment, other compounds which bind the ligand binding pocket, for example, of a vertebrate $H^+$-gated channel, which may be identified by the methods of the present invention, are assayed. In one exemplary embodiment, agonists and/or antagonists are identified. In another exemplary embodiment, an agonist and/or antagonist is manufactured as a medicament for the treatment of conditions relating to activation or inactivation of the $H^+$-gated channel.

PBO-4 Characterization

It has been demonstrated that initiation of the defecation cycle is a highly calcium regulated process, and that calcium spikes in the intestine correlate with the onset of the posterior body contraction (Dal Santo et al., 1999). Therefore, it is believed that the defecation cycle regulated by calcium. The pbo-4 gene encodes a putative $Na^+/H^+$ exchanger that is expressed in the posterior intestine. Without wishing to be bound by theory, it is believed that calcium release in the intestine, through $IP_3$ receptors, results in the activation of PBO-4. Specifically, PBO-4 contains a consensus calmodulin-binding domain that is thought to be inhibitory to transport activity. Therefore, to activate PBO-4, $Ca^{2+}$ would bind the calmodulin site, thereby releasing inhibition and allowing proton transport, hi an exemplary embodiment, the secretion of $H^+$ by PBO-4 from the intestine, in a calcium dependent manner, PBO-4 is assayed for calcium binding and proton transport activity.

The posterior body contraction occurs via a calcium-regulated mechanism. The cloned and characterized pbo-4 gene, which encodes a $Na^+/H^+$ exchanger, is expressed on the basolateral surface of the posterior intestinal cells, juxtaposed to the posterior body wall muscles. Utilizing caged protons, it has been demonstrated that acidification of the pseudocoelomic space, which separates the intestine from the body wall muscles, was sufficient to activate the posterior body contraction in vivo. These results suggest that PBO-4 $Na^+/H^+$ transport activity is required to activate the posterior body contraction. Importantly, the identification of the PBO-5/8 receptor confirms that $H^+$ ions function as a primary transmitter in *C. elegans*. Furthermore, these results demonstrate that $Na^+/H^+$ exchangers can function as a regulated $H^+$ release mechanism that mediates cellular signaling.

pbo-4 Mutations:

| Allele | Nucleotide Change | Protein Change |
|---|---|---|
| Sa300 | GGA → AGA | G318R |
| n2658 | GGTATTAA(Δ548 bp) GACAC | Deletion of the C-terminus |
| ok583 | GCGACTCA (Δ1.702 Kb) aatttt | Deletion of TM3-TM12 |
| ok10 | GCA → GAA | A717D . . . 5 aa . . . Stop |

PBO-8 Behavioral Characterization

In another exemplary embodiment, a deletion library is screened to identify an allele, for example, an allele of pbo-8. Optionally, RNAi technology may be used to knock out expression of PBO-8 or an ortholog/paralog identified in another organism. Any assay known in the art may be used to study a PBO-4, PBO-5, and/or PBO-8 ortholog/paralog, for example, RNAi technology, see U.S. Patent Applications 20030153519, 20030175772, 60/528,567, 60/518,856.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

All references, including sequence accession numbers, publications, patents, and patent applications, cited herein are hereby incorporated by reference to the same extent as if each reference were individually and specifically indicated to be incorporated by reference and were set forth in its entirety herein.

REFERENCES

Beg, A. A., and Jorgensen, E. M. (2003). EXP-I is an excitatory GABA-gated cation channel. Nat Neurosci 6, 1145-1152.

Bertrand, B., Wakabayashi, S., Ikeda, T., Pouyssegur, J., and Shigekawa, M. (1994). The $Na^+/H^+$ exchanger isoform 1 (NHE1) is a novel member of the calmodulin-binding proteins. Identification and characterization of calmodulin-binding sites. J Biol Chem 269, 13703-13709.

Betz, H. (1990). Ligand-gated ion channels in the brain: the amino acid receptor superfamily. Neuron 5, 383-392.

Brejc, K., van Dijk, W. J., Klaassen, R. V., Schuurmans, M., van Der Oost, J., Smit, A. B., and Sixma, T. K. (2001). Crystal structure of an ACh-binding protein reveals the ligand-binding domain of nicotinic receptors. Nature 411, 269-276.

Chalfie, M., Tu, Y., Euskirchen, G, Ward, W. W., and Prasher, D. C. (1994). Green fluorescent protein as a marker for gene expression. Science 263, 802-805.

Counillon, L., and Pouyssegur, J. (2000). The expanding family of eucaryotic Na(+)/H(+) exchangers. J Biol Chem 275, 1-4.

Croll, N. A. (1975). Behavioural analysis of nematode movement. Adv Parasitol 13, 71-122.

Dal Santo, P., Logan, M. A., Chisholm, A. D., and Jorgensen, E. M. (1999). The inositol trisphosphate receptor regulates a 50-second behavioral rhythm in C. elegans. Cell 98, 757-767.

Davies, P. A., Wang, W., Hales, T. G, and Kirkness, E. F. (2003). A novel class of ligand-gated ion channel is activated by Zn2+. J Biol Chem 278, 712-717.

Engel, A. G, Ohno, K., Milone, M., Wang, H. L., Nakano, S., Bouzat, C, Pruitt, J. N., 2nd, Hutchinson, D. O., Brengman, J. M., Bren, N., et al. (1996). New mutations in acetylcholine receptor subunit genes reveal heterogeneity in the slow-channel congenital myasthenic syndrome. Hum Mol Genet 5, 1217-1227.

Karlin, A., and Akabas, M. H. (1995). Toward a structural basis for the function of nicotinic acetylcholine receptors and their cousins. Neuron 15, 1231-1244.

Leonard, R. J., Labarca, C. G., Charnet, P., Davidson, N., and Lester, H. A. (1988). Evidence that the M2 membrane-spanning region lines the ion channel pore of the nicotinic receptor. Science 242, 1578-1581.

Liu, D. W., and Thomas, J. H. (1994). Regulation of a periodic motor program in C. elegans. J Neurosci 14, 1953-1962.

Maruyama, I. N., Rakow, T. L., and Maruyama, H. I. (1995). cRACE: a simple method for identification of the 5' end of mRNAs. Nucleic Acids Res 23, 3796-3797.

McIntire, S. L., Jorgensen, E., and Horvitz, H. R. (1993a). Genes required for GABA function in Caenorhabditis elegans. Nature 364, 334-337.

McIntire, S. L., Jorgensen, E., Kaplan, J., and Horvitz, H. R. (1993b). The GABAergic nervous system of Caenorhabditis elegans. Nature 364, 337-341.

Orlowski, J., and Grinstein, S. (1997). $Na^+/H^+$ exchangers of mammalian cells. J Biol Chem 272, 22373-22376.

Ortells, M. O., and Lunt, G. G. (1995). Evolutionary history of the ligand-gated ion-channel superfamily of receptors. Trends Neurosci 18, 121-127.

Palma, A., Li, L., Chen, X. J., Pappone, P., and McNamee, M. (1991). Effects of pH on acetylcholine receptor function. J Membr Biol 120, 67-73.

Pasternack, M., Bountra, C, Voipio, J., and Kaila, K. (1992). Influence of extracellular and intracellular pH on GABA-gated chloride conductance in crayfish muscle fibres. Neuroscience 47, 921-929.

Thomas, J. H. (1990). Genetic analysis of defecation in Caenorhabditis elegans. Genetics 124, 855-872.

Treinin, M., and Chalfie, M. (1995). A mutated acetylcholine receptor subunit causes neuronal degeneration in C. elegans. Neuron 14, 871-877.

Unwin, N. (1993). Nicotinic acetylcholine receptor at 9 A resolution. J Mol Biol 229, 1101-1124.

Wakabayashi, S., Bertrand, B., Hceda, T., Pouyssegur, J., and Shigekawa, M. (1994). Mutation of calmodulin-binding site renders the $Na^+/H^+$ exchanger (NHE1) highly H(+)-sensitive and $Ca^{2+}$ regulation-defective. J Biol Chem 269, 13710-13715.

Wakabayashi, S., Ikeda, T., Iwamoto, T., Pouyssegur, J., and Shigekawa, M. (1997). Calmodulin-binding autoinhibitory domain controls "pH-sensing" in the $Na^+/H^+$ exchanger NHE1 through sequence-specific interaction. Biochemistry 36, 12854-12861.

Waldmann, R., Champigny, G., Bassilana, F., Heurteaux, C, and Lazdunski, M. (1997). A proton-gated cation channel involved in acid-sensing. Nature 386, YT1-XI1.

Waldmann, R., Champigny, G., Lingueglia, E., De Weille, J. R., Heurteaux, C, and Lazdunski, M. (1999). H(+)-gated cation channels. Ann N Y Acad Sci 868, 67-16.

What is claimed is:

1. A method of screening a candidate compound, the method comprising:
   (a) introducing a nucleic acid sequence that encodes an amino acid sequence having 80% identity to PBO-4 (SEQ ID NO:8) into a host cell;
   (b) expressing the nucleic acid sequence to produce a $H^+/Na^+$ exchanger in the host cell;
   (c) contacting the host cell with a candidate compound; and
   (d) screening for activation or inhibition of the $H^+/Na^+$ exchanger by the candidate compound.

2. The method of claim 1, further comprising:
   (a) introducing a nucleic acid sequence encoding PBO-5 (SEQ ID NO:2 or SEQ ID NO:6) into a host cell; and
   (b) expressing the nucleic acid sequence to produce a $H^+/Na^+$ exchanger in the host cell.

3. The method of claim 1, further comprising:
   (a) introducing a nucleic acid sequence encoding PBO-8 (SEQ ID NO:3 or SEQ ID NO:4 or SEQ ID NO:7) into a host cell; and
   (b) expressing the nucleic acid sequence to produce a $H^+/Na^+$ exchanger in the host cell.

4. The method of claim 1, further comprising producing the candidate compound.

5. The method of claim 1, further comprising identifying a compound that prevents binding of HEPES to the ligand-gated cation channel.

* * * * *

SEQUENCE LISTING

```
<160> NUMBER OF SEQ ID NOS: 8

<210> SEQ ID NO 1
<211> LENGTH: 8746
<212> TYPE: DNA
```

<213> ORGANISM: Caenorhabditis elegans

<400> SEQUENCE: 1

```
atgactcgat tatcaatttt acaacacctg ttaacatttt taatactttc taaaatcaat        60
gcgacatcaa cgacagaatc atattttgat agcagtgaag aagctccgaa tgttttatta       120
aatcatctaa acaacgaatc tgaaggtgaa gagctcactc aaataaatga cactcagcct       180
gcctttgtcc caggttcttc aaaacgcctt actgaatact tactttcaag acacaatttg       240
aatgctccgc cgatggatt attatatgtg gagtacgaac ttgaactggt tcatattttg       300
ggaattgatg aattgaagca acaatgacc gttctcatat atgttgatga gcattgggtc        360
gatcctagtc ttacctggga tccagcactt tttggaggaa tcacgaaaac ttggattcca       420
ttagacaaga tttgggtccc agatatcata gttttcaaca tgctggcaca tgaggatctt       480
ctctccgctg ttcgagcacc tgctcgaatt cactataatg gtaccattgt tgcgagtcac       540
ccggcggtgc atacagtgtc ttgcgaaatc aacataagac attttccact tgacgatcaa       600
cgatgcgcaa ttgagattgc ttcatgggct tatggtcaag aaaaaattcg acttcatgct       660
cacacagatc actctttaga acactacaag cgaaacgagg aatggcattt gctgaatctc       720
aatgtttcag aagaaaaata cgaacacgag ggtgtcgagg tgtcggaagt taaatttgaa       780
atttccctga acggcggcc actattctat atggtaacat tgacgttcc tagttacata        840
atgtgtgcga tatctgtcgt gggactgttt gctcggtttt ctacaactgg ggaaagagaa       900
gaaagattca cattaggagt aactgcaatc ttgaccatgg cagttctctc tttggtggtc       960
agtgagaaag ttccgcacag ctctacacat gtgcctttat tggttgctta ttttctgttc      1020
aatatggtca tcgtgtcgat tgctgcaatg acaactggaa tcgtcatgaa agttcatcgt      1080
ttgggacgat atggcgacga gccaagtgat ttctggatga ggtgtttctt attgaaacca      1140
gtgtttcgaa caagtaaccg ccgaaagtat cgaatgaatc cagaagaacc gactcaagtg      1200
atacttgttt ctgaagcaaa aaatggagaa gttctcacaa agaaatcaac ggagctcaat      1260
ggaaccgtgg taaaagaaat tatgcttttca agccgtctag aagctctaga agagtatatt      1320
cgcaaaatgg taaaccgatg tgaaacgatt aagtgggagc ttgacgaaat cgacgcagcc      1380
gaaaacatag agctagttcg ccgccgatca acaaatggat atgttcgaat tcggaacgt       1440
ttggatattt tgttcatgtt tcttttttctg tcgactgtaa ctatccccgt ggctgtgctg      1500
ttttatttaa cttgaatgac tcgattatca atttttacaac acctgttaac attttttaata     1560
ctttctaaaa tcaatgcgac atcaacgaca gaatcatatt ttgatagcag tgaagaagct      1620
ccgaatgttt tattaaatca tgtgagtttta atattcctaa cataaaatgt ttctaataat     1680
tatctaagaa acaataaaat agtacgtttt ttcagctaaa caacgaatct gaaggtgaag      1740
agctcactca aataaatgac actcagcctg cctttgtccc aggtaacttg ttttttgattc     1800
ctgtagttta agtaaattgc atgacttttc gatagaccta agtatttttt gaaatgttgc      1860
aactttcaac ccctctggaa agcgagaaga atgatttcg gaaaacaaat gtattcttcc       1920
cttttctcct aaccaaaaac gtgacctaaa gaacaagaat ccacatggag cgtccacact     1980
aatttgaatt tggggtgctg ttacgtagtc aatgatcatt tcatttttggt ggggtctcat    2040
tttaaacatt ttacctaaat tgaccaacga ctgctggaga gggttgatca aaacatataa     2100
tgggaaatat catatttgga gaaacaacaa caagactaat catgcagatt cggttgattc     2160
tagaaatcta ggtgcgcagt taaaggtgga gtaccgaaat ctgggaaaat tttttaaatg     2220
attttaaatt tgcccctgaa atcgaaaaac tgcgtgcaaa aaataaaaaa aaaatttccc      2280
```

```
tgatttttaag cttgaaatcg cgaattttat ttactttccc attactttttt tttcaaatgc    2340 gcgcccaaat aaattctcca tggagcgcgt aggggagtg aaaataggta gagaaaatta      2400
aatgaagcag acgcgctcca gggggaattc atttgggcgc gcatttcaaa aatctcactg    2460
gggacgcaaa tgaaattcgc gatttcaagc tcaaatatta aatcagggag attttttga      2520 ttttttttag atagatattt ggattcagag acaaatttga agtcatttaa aaacatttct    2580
tagactttgc tgctccactt ttaatattca gtaaatcaac attttcgcgt atccaaagta    2640
aaagttaaag tgtaaccaat acacacattt ctttgtgaca cctcaaccag tgctcacctc    2700
atgcgacctc atcctccgca gctcctatcg ccactcaaaa agccccatta tcggttttga    2760
tttgtgggcc acattgtgtt gcctcttcgc acactctcaa gctaactaca ttctgtcaaa    2820
aaaaatcttt tttgaagttc tcaatatttt tatggcataa ctgggagatg aaaacgaagc    2880
atttatagaa ctgaatgtac aattatcatt tacgtgattt acaggttctt caaaacgcct    2940
tactgaatac ttactttcaa gacacaattt gaatgctccg cccgatggat tattatatgt    3000
ggagtacgaa cttgaactgg ttcatatttt gggaattgat gaattgaagc aaacaatgac    3060
cgttctcata tatgttgatg agcattgggt cgatcctagt cttacctggg atccagcact    3120
ttttggagga atcacgaaaa cttggattcc attagacaag atttgggtcc cagatatcat    3180
agttttcaac atgtgagttg atagcctttt gtcaaaacta accagaattt caaattatta    3240
aaatgaaatc tacggaatta gacttccatg cgaaaatata atacatgtgc actctaacaa    3300
ttataattag ctatttggcg gaaggaaggg tgtcacaaca accaaacata aaaattagga    3360
tgagaggaaa agggaagaaa cagagaaaca tagagatgtg gaaacgatag gatggtgttt    3420
cccccaaaaa catttaaaa caatattggt ggcttctcaa gccccaatc gtctaaaggg      3480 taaaatctaa caggctggca catgaggatc ttctctccgc tgttcgagca cctgctcgaa    3540
ttcactataa tggtaccatt gttgcgagtc acccggcggt gcatacagtg tcttgcgaaa    3600
tcaacataag acattttcca cttgacgatc aacgatgcgc aattgaggtt agtcaatgaa    3660
aaattaaagt aacaattttt gaacaaaagt acaaagtaag gttgccaggt taccaaataa    3720 cttaaaata actgaattta caaatccaag acatcattct gataattatt tgtatacaca    3780
taatacccaa attaacgaaa caacgcgtag taaacataaa atataaaaaa ggtgataact    3840
aattaaacac cagattcgag cggttgtgat tttgtcaagt cggcaaaatg tatgatgata    3900
gctgaaaatt agcttttttt gaggaatatt ttggattacg aagtattcaa caaatatcca    3960
aacaaagcaa taagtcaaac ttacaggtgg agtaccgaaa tctgggaaat attttcaatt    4020
gacttcaaat tgtcccctg attccgaata tctatgtgaa aaatttcgag aaaaattacc      4080
atgatttaat atctaattgt aagcttggaa tcacaaattt acgtggtgtc aggctgtctt    4140
attgcggttt gatctacaaa aaatgcggga atcttttgcc ctagactgca atactaatag    4200
aggctgcaag actataattt tcgattggcc cgtaagacta atagggtgc aaaactaata      4260 gaggctgcaa gactaataga ggaaatacgg aaattataaa attagggaat tttttcaca      4320 tcaatgtttg gaatcagggg caaatttggt gtcgattaaa atttgttccc agatttcggc    4380
agcccacctt caaacgcaac atacgctcaa acaggagaaa acaaacgttt atgacctttc    4440
attgaaaatt tgttacagat tgcttcatgg gcttatggtc aagaaaaaat tcgacttcat    4500
gctcacacag atcactcttt agaacactac aagcgaaacg aggaatggca tttgctgaat    4560
ctcaatgttt cagaagaaaa atacgaacac gagggtgtcg aggtgtcgga agttaaatttt    4620 gaaatttccc tgaaacggcg ccactattc tatatggtaa cattgacgtt tcctagttac      4680
```

```
ataatgtgtg cgatatctgt cgtgggactg tttgctcggt tttctacaac tggggaaaga    4740
gaagaaagat tcacattagg agtaactgca atcttgacca tggcagttct ctctttggtg    4800
gtcagtgaga aagttccgca cagctctaca catgtgcctt tattgggtca gttaactatt    4860
acttcatagg aaataaaaac tatatctatc tcgtttccag ttgcttattt tctgttcaat    4920
atggtcatcg tgtcgattgc tgcaatgaca actggaatcg tcatgaaagt tcatcgtttg    4980
ggacgatatg gcgacgagcc aagtgatttc tggatgaggt gtttcttatt gaaaccagtg    5040
tttcgaacaa gtaacgtgag ttgtgtatgt taaaatttgt ttgtaactgt tcaaaaatta    5100
tagcgccgaa agtatcgaat gaatccagaa gaaccgactc aagtgatact tgtttctgaa    5160
gcaaaaaatg gagaagttct cacaaagaaa tcaacggagc tcaatggaac cgtggtaaaa    5220
gaaattatgg tataaccaat caataaaaaa caaaaaaaaa cttttgaaat gaacattttc    5280 agcttttcaag ccgtctagaa gctctagaag agtatattcg caaaatggta aaccgatgtg    5340
aaacgattaa ggtgagcaaa atcttgcatt aaaagtaaaa taactactca tgtggcgctg    5400
aactaaccaa ttatcatagt aatccgcttc aaaactatct tgttttgttt aaattcaaat    5460
acaaaaagtt gggagaactc agtttacccc tatcataatt tcggtaaccc actgcaactt    5520
ttttcacacg agggacgagg caaagccggt tctaggccat ggccgaggat ccgtcaagtt    5580
tcagcggcaa tttatcttgc cttgttttcc gcttgttttt tgtggttttt atttgatttt    5640
ttctccgttt ttcttactaa aactgataaa taaactttt taagagttaa aacaatttcc    5700
atacaaacaa attttttgtt atttccgaca agtagtgctg aaagttgtga ggtaagtatc    5760
atcgattgtg gtgatgcaaa ccctaatttt ttttccaagc atgataaatg aataagctga    5820
ttagatgaac aagaccggca aaaagttttt gaattttgc aaaataaat tcaattttta    5880 ctccaaaaaa tcacgatttt tttaaccaaa aaatgaaatt ttaaaaacct caaaactttt    5940
ttggttgtcg ttatgaaaat caaatacatt tagcatctaa gcagcttatt tgaagaaggt    6000
taggtttttg cattcccgca atcgatgata catacttacc tcacaacttt cagcgctagg    6060
tacttgtcga attaacacat tttttttcat atggaaattg ttttaacatc tgagaaaata    6120
tttatttatc agttttagta aggaaacacg aaaaaaatca cataaaccac aaaaaacaag    6180
cggaagcaag gcaagataaa ttgccgctga aacttgttgg attctcggcc atggcgcctc    6240
gtccctcgtg cgaaaaaagt ttcagtgaaa ccggccagaa acattcctat ttttcctacg    6300
atttttgtat tcgaattttt attcggatat ttgtgttcga acgttgtaga agtgtatgtg    6360
aaaatgctct aaatttctca aatagccaaa agttttcgtg aattaggcaa tttaccagaa    6420
cacttttttt aaaaattaat ctatgcgacc tgataactga agctcagaaa tcatgatcct    6480
cattccgagt ttccggtgat aacgtgtctt gcgacacaca cttaattgc gttcacccac    6540 ttcttgtgtg ctttgtttct ttttctttg cgctcatctt cttcatcgtt tctatctgtc    6600
atttgcacac gcattgagta gtccacacac acaagactgc tgaatgtaga gagccacaca    6660
caacaccaac tgtgcccata aattgttgaa tgtgtctttt ccgctgttag aagccggcgg    6720
aatgggaaga caagcaaatc cacagaaagg tggttcagta ccttacgcaa gtagctggtt    6780
tttgttcagt aatttagaaa tcaagaaact tcgcggaatt aaagaatttt caaaatagct    6840
tgaaaacatt caataaaccct ttatgctatt aaggatgcca ataagttaca gataaaaatt    6900
cccagtatcc tctatcgcca ttagattctt accagtatcc tctgttgcca ttagattctt    6960
attactttat gggtatatgg tgtatgaagt atgatatttt atttaaaaaa ttttcatgtg    7020
cttttgctca gcccaggttc ttttacagga ggttttttaaa gttttttgtcc gttctgattt    7080
```

-continued

```
tagctcacgt aaacattcag aaaattaaaa gggtgtagaa tttgtggtta ttttgcttaa    7140
atagactaaa actggtccaa aaacatcaag tttcataatg aaactttaaa acaaatgcac    7200
aaattttttt tatggcggat caaagggggct ttttttaaaa acttttctga tattattcct   7260
ttcatccatg gtaatttatc tcgcataaac tcgttgattg agagacattt taagcccatt    7320
ggcagccaat attgatcatt ttttcgatac ctatgggaca catttattcg tttccggtgg    7380
ggcacgaaaa cgttttcggt ggggcacgga aatgtaaatt ttatttgtgc cccactgtct    7440
gaaaatgttc ttaaataaat aaaagacgc ctaataaaaa ccataatgtt cattaaaaag     7500
tgataattga atacaaatca agttccagac gctgcgacgc cgagaaattt tacagaaatt    7560
ttgcttttag ctgaaaatgg gcttttttt tcagagcttt gaaccgccat aacttttttt     7620
ttgagaaatt ttcaaaaagt ttcattacga aatttggtag tatttgatca ctttgggtct    7680
aaaatgggaa agtatcagat ttcggtagtc catcttttaaa aacatgtttg atacgtattt   7740
tgaattgaat ctgagtttat taactaaaag aagaaaaata aacaaataaa gcgagacgag    7800
ttcaactcga gtgaaagttg aaaaaaaaat tataatgcta ttttgccatt ttagcaccat    7860
ttaaattgtt tttgatcatt tttcgatagg atgtactgca ccctaaaaat ttgacctgat    7920
caaaatgtgt aaatactatg ataatataaa aattgttcaa acaacttttt ttaaagtata    7980
acaaatcttc gaaatgtttt tcataacaaa caatgtgttt tcattatttt tctacaaaat    8040
aaaaaatttc agacaattaa tttgcttcga agattttttg acgaccgaca aaaatttatt    8100
tgaactaatt tttttcaaac ttttattgaa catatgttct ctgttcatac ttcgttgtaa    8160
attgagcaaa acctattcaa caaacggggt caaatgaaaa taagcaagcg ctgacagaag    8220
cctaaaaaat taatacgtta atctcggtaa atacacatta ggcgatcata agattgaaaa    8280
aaagttaaaa atacagatca tgcttgttaa cacaaatttc cacaaataaa ttaaattgat    8340
aaatgttgac tccctcctcc gggactaatt gaaccgcttg atcattgaat cgggtttaat    8400
tgattaataa tattatttca gtgggagctt gacgaaatcg acgcagccga aaacatagag    8460
ctagttcgcc gccgatcaac aaatggatat gttcgaattt cggaacgttt ggatattttg    8520
ttcatgtttc ttttctgtc gactgtaact atccccgtgg ctgtgctgtt ttatttaact     8580
tgaagaacta gttttgcaat tgccaacaaa gacttctaaa acgggttcta gctgcaatgg    8640
attccaatcg gttttaaaa cactattttt ctcttcaaaa gttaccttt ccttactatt      8700 tggttgtcaa aattacattt atttggaaat tttgtgagtt ttaact                   8746
```

<210> SEQ ID NO 2
<211> LENGTH: 504
<212> TYPE: PRT
<213> ORGANISM: Caenorhabditis elegans

<400> SEQUENCE: 2

```
Met Thr Arg Leu Ser Ile Leu Gln His Leu Leu Thr Phe Leu Ile Leu
1               5                   10                  15

Ser Lys Ile Asn Ala Thr Ser Thr Thr Glu Ser Tyr Phe Asp Ser Ser
            20                  25                  30

Glu Glu Ala Pro Asn Val Leu Leu Asn His Leu Asn Asn Glu Ser Glu
        35                  40                  45

Gly Glu Glu Leu Thr Gln Ile Asn Asp Thr Gln Pro Ala Phe Val Pro
    50                  55                  60

Gly Ser Ser Lys Arg Leu Thr Glu Tyr Leu Leu Ser Arg His Asn Leu
65                  70                  75                  80

Asn Ala Pro Pro Asp Gly Leu Leu Tyr Val Glu Tyr Glu Leu Glu Leu
```

```
                    85                  90                  95
Val His Ile Leu Gly Ile Asp Glu Leu Lys Gln Thr Met Thr Val Leu
            100                 105                 110

Ile Tyr Val Asp Glu His Trp Val Asp Pro Ser Leu Thr Trp Asp Pro
            115                 120                 125

Ala Leu Phe Gly Gly Ile Thr Lys Thr Trp Ile Pro Leu Asp Lys Ile
            130                 135                 140

Trp Val Pro Asp Ile Ile Val Phe Asn Met Leu Ala His Glu Asp Leu
145                 150                 155                 160

Leu Ser Ala Val Arg Ala Pro Ala Arg Ile His Tyr Asn Gly Thr Ile
                165                 170                 175

Val Ala Ser His Pro Ala Val His Thr Val Ser Cys Glu Ile Asn Ile
            180                 185                 190

Arg His Phe Pro Leu Asp Asp Gln Arg Cys Ala Ile Glu Ile Ala Ser
            195                 200                 205

Trp Ala Tyr Gly Gln Glu Lys Ile Arg Leu His Ala His Thr Asp His
            210                 215                 220

Ser Leu Glu His Tyr Lys Arg Asn Glu Glu Trp His Leu Leu Asn Leu
225                 230                 235                 240

Asn Val Ser Glu Glu Lys Tyr Glu His Glu Gly Val Glu Val Ser Glu
                245                 250                 255

Val Lys Phe Glu Ile Ser Leu Lys Arg Arg Pro Leu Phe Tyr Met Val
            260                 265                 270

Thr Leu Thr Phe Pro Ser Tyr Ile Met Cys Ala Ile Ser Val Val Gly
            275                 280                 285

Leu Phe Ala Arg Phe Ser Thr Thr Gly Glu Arg Glu Glu Arg Phe Thr
            290                 295                 300

Leu Gly Val Thr Ala Ile Leu Thr Met Ala Val Leu Ser Leu Val Val
305                 310                 315                 320

Ser Glu Lys Val Pro His Ser Ser Thr His Val Pro Leu Leu Val Ala
                325                 330                 335

Tyr Phe Leu Phe Asn Met Val Ile Val Ser Ile Ala Ala Met Thr Thr
            340                 345                 350

Gly Ile Val Met Lys Val His Arg Leu Gly Arg Tyr Gly Asp Glu Pro
            355                 360                 365

Ser Asp Phe Trp Met Arg Cys Phe Leu Leu Lys Pro Val Phe Arg Thr
            370                 375                 380

Ser Asn Arg Arg Lys Tyr Arg Met Asn Pro Glu Glu Pro Thr Gln Val
385                 390                 395                 400

Ile Leu Val Ser Glu Ala Lys Asn Gly Glu Val Leu Thr Lys Lys Ser
                405                 410                 415

Thr Glu Leu Asn Gly Thr Val Val Lys Glu Ile Met Leu Ser Ser Arg
            420                 425                 430

Leu Glu Ala Leu Glu Glu Tyr Ile Arg Lys Met Val Asn Arg Cys Glu
            435                 440                 445

Thr Ile Lys Trp Glu Leu Asp Glu Ile Asp Ala Ala Glu Asn Ile Glu
            450                 455                 460

Leu Val Arg Arg Arg Ser Thr Asn Gly Tyr Val Arg Ile Ser Glu Arg
465                 470                 475                 480

Leu Asp Ile Leu Phe Met Phe Leu Phe Leu Ser Thr Val Thr Ile Pro
                485                 490                 495

Val Ala Val Leu Phe Tyr Leu Thr
            500
```

-continued

```
<210> SEQ ID NO 3
<211> LENGTH: 364
<212> TYPE: PRT
<213> ORGANISM: Caenorhabditis elegans

<400> SEQUENCE: 3

Met Gly Leu Val Asn Cys Phe Val Ser Arg Ala Pro Leu Leu Gln His
1               5                   10                  15

Ile Leu Pro Asp Leu Ser Leu Cys Ser Ser Gln Lys Leu Ile Leu Ile
            20                  25                  30

Thr Gly Pro Val Leu Phe Phe Asn Met Gln Cys Ser Phe Leu Thr Ile
        35                  40                  45

Phe Ile Phe Ile Thr Thr Val Thr Val Gly Val Ala Glu Phe Ser Glu
    50                  55                  60

Gln Tyr Gln Gly Ser Ser Ser Arg Leu Thr Arg His Leu Leu Glu Lys
65                  70                  75                  80

His Asn Lys Cys Ser Pro Pro Asp Gly Arg Val Asp Ile Ser His Asn
                85                  90                  95

Ile Glu Leu Val His Ile Ile Gly Ile Asn Glu Leu Asn Gln Asn Met
            100                 105                 110

Gln Val Leu Val Tyr Ile Val Gln Gln Trp Thr Asp Ala Ser Leu Ser
        115                 120                 125

Trp Lys Val Glu Glu Phe Arg Gly Ile Lys His Thr Trp Leu Pro Glu
130                 135                 140

His Ser Ile Trp Ile Pro Asp Ile Ile Val Phe Asn Thr Leu Glu His
145                 150                 155                 160

Lys Met Leu Leu Glu Ala Val Arg Ser Pro Ile Lys Val Ser Tyr Thr
                165                 170                 175

Gly Glu Val Thr Tyr Ala Tyr Pro Ala Ile Tyr Thr Val Leu Cys Gln
            180                 185                 190

Ile Gly Ile Ala Thr Phe Pro Phe Asp Gln Val Tyr Val Gln Phe
        195                 200                 205

Ala Ser Trp Ala Tyr Asp Glu Asp Lys Ile Leu Leu Asn Ala Ser His
    210                 215                 220

Lys Pro Leu Leu Lys Asn Tyr Ser Pro Asn Glu Glu Trp Ala Leu Gln
225                 230                 235                 240

Val Ser Cys Tyr Lys Gly Phe Gly Arg Phe Leu Asn Phe Leu Lys Thr
                245                 250                 255

Asp Val Asp Met Ala Arg Lys Gly Tyr Glu His Glu Glu Thr Val Val
            260                 265                 270

Ser Glu Ile Ile Tyr Tyr Ile Lys Val Ala Arg Lys Pro Phe Tyr Tyr
        275                 280                 285

Leu Ile Ser Leu Val Val Pro Ser Tyr Ile Ile Cys Val Leu Ser Ile
    290                 295                 300

Ala Gly Leu Phe Ala Arg Phe Ser Thr Lys His Glu Arg Gln Glu Arg
305                 310                 315                 320

Phe Thr Leu Gly Val Thr Ala Ile Leu Ser Met Ala Val Leu Ser Leu
                325                 330                 335

Val Val Thr Glu Lys Val Pro His Ser Ser Glu Asn Val Pro Leu Leu
            340                 345                 350

Ser Lys Phe Phe Phe Leu Arg Thr Lys Leu Met Phe
        355                 360

<210> SEQ ID NO 4
<211> LENGTH: 422
```

<212> TYPE: PRT
<213> ORGANISM: Caenorhabditis elegans

<400> SEQUENCE: 4

```
Met Gln Cys Ser Phe Leu Thr Ile Phe Ile Phe Ile Thr Thr Val Thr
1               5                   10                  15

Val Gly Val Ala Glu Phe Ser Glu Gln Tyr Gln Gly Ser Ser Ser Arg
            20                  25                  30

Leu Thr Arg His Leu Leu Glu Lys His Asn Lys Cys Ser Pro Pro Asp
        35                  40                  45

Gly Arg Val Asp Ile Ser His Asn Ile Glu Leu Val His Ile Ile Gly
    50                  55                  60

Ile Asn Glu Leu Asn Gln Asn Met Gln Val Leu Val Tyr Ile Val Gln
65                  70                  75                  80

Gln Trp Thr Asp Ala Ser Leu Ser Trp Lys Val Glu Glu Phe Arg Gly
                85                  90                  95

Ile Lys His Thr Trp Leu Pro Glu His Ser Ile Trp Ile Pro Asp Ile
            100                 105                 110

Ile Val Phe Asn Thr Leu Glu His Lys Met Leu Leu Glu Ala Val Arg
        115                 120                 125

Ser Pro Ile Lys Val Ser Tyr Thr Gly Glu Val Thr Tyr Ala Tyr Pro
    130                 135                 140

Ala Ile Tyr Thr Val Leu Cys Gln Ile Gly Ala Thr Phe Pro Phe
145                 150                 155                 160

Asp Asp Gln Val Cys Lys Ile Arg Phe Ala Ser Trp Ala Tyr Asp Glu
                165                 170                 175

Asp Lys Ile Leu Leu Asn Ala Ser His Lys Pro Leu Leu Lys Asn Tyr
            180                 185                 190

Ser Pro Asn Glu Glu Trp Ala Leu Gln Asp Val Asp Met Ala Arg Lys
        195                 200                 205

Glu Tyr Glu His Glu Glu Thr Val Val Ser Glu Ile Ile Tyr Tyr Ile
    210                 215                 220

Lys Val Ala Arg Lys Pro Phe Tyr Tyr Leu Ile Ser Leu Val Val Pro
225                 230                 235                 240

Ser Tyr Ile Ile Cys Val Leu Ser Ile Ala Gly Leu Phe Ala Arg Phe
                245                 250                 255

Ser Thr Lys His Glu Arg Gln Glu Arg Phe Thr Leu Gly Val Thr Ala
            260                 265                 270

Ile Leu Ser Met Ala Val Leu Ser Leu Val Val Thr Glu Lys Val Pro
        275                 280                 285

His Ser Ser Glu Asn Val Pro Leu Leu Ile Val Tyr Met His Phe Ile
    290                 295                 300

Ile Val Met Val Thr Ile Ala Thr Ile Leu Thr Ser Thr Val Met Arg
305                 310                 315                 320

Val His Ala Lys Gly Phe Arg Thr His Phe Leu Ser Pro Pro Asn Trp
                325                 330                 335

Ile Arg Lys Val Leu Leu Ile Ala Arg Lys His Ala Asn Phe Phe Gln
            340                 345                 350

Gln His Gly Lys Val Tyr Met Asp Ile His Thr Thr Ala Glu Gln Trp
        355                 360                 365

Gly Glu Val Ser Arg Arg Met Asp Tyr Leu Leu Ala Ser Val Phe Ile
    370                 375                 380

Ile Ile Ile Ser Thr Pro Thr Leu Tyr Leu Phe Tyr Met Cys Phe Gln
385                 390                 395                 400
```

Met Asp His Ala Thr Ala Glu Arg Val Leu Leu Glu Asn Ala Lys Arg
                405                 410                 415

Arg Asp Gln Leu Tyr Tyr
            420

<210> SEQ ID NO 5
<211> LENGTH: 4116
<212> TYPE: DNA
<213> ORGANISM: Caenorhabditis elegans

<400> SEQUENCE: 5

| | | | | | |
|---|---|---|---|---|---|
| atggggctcg | ttaattgttt | tgtgagccgg | gctccgcttc | tccaacacat | tttgcctgat | 60 |
| ctctcattgt | gctcttctca | aaagctcata | ctcatcacag | gaccagtgtt | attttcaac | 120 |
| atgcagtgtt | cttttctaac | catattcatc | ttcatcacaa | cggtcacagt | tggggtagca | 180 |
| gagttttcag | aacaatacca | agggtcgtct | agcaggttga | caagacattt | actggaaaaa | 240 |
| cataacaaat | gttcacctcc | agatggggag | gtagacattt | cgcacaacat | agaacttgtt | 300 |
| catattattg | gaatcaatga | gctcaaccaa | acatgcaag | ttttggttta | tattgtacaa | 360 |
| caatggaccg | atgcgtcgtt | aagctggaaa | gttgaagagt | tcgaggaat | aaaacacaca | 420 |
| tggcttccag | aacattcgat | ttggattccg | gatattattg | ttttcaatac | acttgagcac | 480 |
| aagatgctcc | tagaagctgt | tcgatcaccg | atcaaagttt | cttataccgg | tgaggtcacc | 540 |
| tatgcatacc | cagcaattta | cacagtgctt | tgtcaaattg | gaattgccac | ttttccgttt | 600 |
| gatgatcaag | tatacgttca | gtttgcttcc | tgggcttacg | atgaggataa | gattttgctc | 660 |
| aatgcatcac | ataaaccgct | actcaaaaac | tactctccca | acgaggaatg | ggcacttcag | 720 |
| gtcagctgtt | acaagggttt | tggaagattt | ttgaactttt | tgaaaacaga | tgtagacatg | 780 |
| gcacgaaaag | aatacgagca | tgaagaaact | gttgtcagtg | agataatcta | ttacatcaaa | 840 |
| gttgcccgca | aaccgttcta | ctaccttatc | agtcttgtgg | tacctagtta | tattatatgt | 900 |
| gtactatcaa | ttgcgggact | gttcgccagg | ttttcaacaa | acatgaaag | acaggaacga | 960 |
| ttcacacttg | gagtcactgc | aattctcagt | atggctgtct | tatcattggt | tgttactgaa | 1020 |
| aaggtaccac | atagttcgga | aaatgttcca | ctcctcagta | agtttttttt | cttaagaaca | 1080 |
| aagttgatgt | tttaaatggg | gctcgttaat | tgttttgtga | gccgggctcc | gcttctccaa | 1140 |
| cacattttgc | ctgatctctc | attgtgctct | tctcaaaagc | tcatactcat | cacaggacca | 1200 |
| gtggtgccct | cattcaggtt | cacacgtttt | ccaaaatatt | cttcagactg | tttttagtt | 1260 |
| attttcaac | atgcagtgtt | cttttctaac | catattcatc | ttcatcacaa | cggtcacagt | 1320 |
| tggggtagca | gagttttcag | aacaatacca | aggtattact | ttgataattg | aaagtttata | 1380 |
| aattatttca | tttacagggt | cgtctagcag | gttgacaaga | catttactgg | aaaaacataa | 1440 |
| caagtgagaa | aacattaaca | ctcaataaat | accaaaattc | tttttttttc | cagatgttca | 1500 |
| cctccagatg | ggagggtaga | catttcgcac | aacatagaac | ttgttcatat | tattggaatc | 1560 |
| aatgagctca | accaaaacat | gcaagttttg | gtttatattg | tacaagtaag | ttgatagctg | 1620 |
| ttttgagggg | tcttctctaa | aacctataaa | atattgcgct | caatgagttc | aacattatac | 1680 |
| agttaaagtg | gcagaaaatc | agaaaaactg | cagaaaaaat | gtatatatcg | tattttact | 1740 |
| tttatttta | tttttagtaa | gactatttt | caatgggtaa | agttacggat | tgtacttata | 1800 |
| cttatacttt | taacattttt | acagaactat | cgttttctc | agactgacaa | tatcaagtaa | 1860 |
| tttacagaac | gaaaaattta | gtgggaatta | ttgttaaagt | atatcactc | cataagaact | 1920 |
| ataaattatt | caaaatgtga | aaacaattc | gaaatctaga | aatcttccag | atgttcaaac | 1980 |

```
taattgtttt gcaaaaaatt acgaccaatg aatttgttaa acaattttgt tttatttca      2040
gcaatggacc gatgcgtcgt taagctggaa agttgaagag tttcgaggaa taaaacacac    2100
atggcttcca gaacattcga tttggattcc ggatattatt gttttcaata cgtatgttgg   2160
acttgaaaat tgagaaatta caataaaaca ttgtataatg gaatttgcaa tgtcgaatct   2220
gggtctgata cttgtttttt taagtcatat ttttttttca attttaattt taaaaacaag   2280
tcaacaggca aaataacagt aattattaat taattcacat cagtatcagt aatgtatcag   2340
aaaatggaaa aatttgaaca tttcaacttt gattttgtc aattttctta aattaaaatc    2400
aactttcaaa tatgcactat catttaaag tttttgatct gaaaaaatac cggaaattt     2460
tcagacttga gcacaagatg ctcctagaag ctgttcgatc accgatcaaa gtttcttata   2520
ccggtgaggt cacctatgca tacccagcaa tttacacagt gctttgtcaa attggtgagt   2580
gtttccagtc acgtataaat tgggttctg gaaaaggga tgtctaatgg attaatgata     2640
aatgagtttt caaccacatt ccaagctttt ccattatccc ttggcttgtc tcatttgcgg   2700
gtgcatccta tcaattatct tagaacaaca tctaagcgca gtttcatttt cttatctt    2760
tcccgtatta ttgagagcaa gaaatgatgc gtttttccgc atgatcataa atctttcagg  2820
aattgccact tttccgtttg atgatcaagt atgtaagatt cgtgtaagtt caaaatgtct   2880
cgattaaaaa ggggattatt tgaagacgtt cagtttgctt cctgggctta cgatgaggat   2940
aagattttgc tcaatgcatc acataaaccg ctactcaaaa actactctcc caacgaggaa   3000
tgggcacttc aggtcagctg ttacaagggg tttggaagat ttttgaactt tttgaaaaca   3060
gtaggtgcaa atagaattag acatgttaaa attttagaaa aactttgaac gtcataaaat   3120
ttaggagaaa tgtttcacaa aaattgtta caaacatttt tacaatgacg atttaatgcg    3180
gagcaattca aaatgttcaa attgaaactt attacaagat atatttagac aaagtttgat   3240
tcaagaattg gtcaacaaat ttaagaat tttatgaaat atggtttgtt ttttgagttc    3300
ttctaatggt tttaattctg ccttgtacta agctttcttt ccaggatgta gacatggcac   3360
gaaaagaata cgagcatgaa gaaactgttg tcagtgagat aatctattac atcaaagttg   3420
cccgcaaacc gttctactac cttatcagtc ttgtggtacc tagttatatt atatgtgtac   3480
tatcaattgc gggactgttc gccaggtttt caacaaaaca tgaaagacag gtaattgtgg   3540
tttgatttga ttgttgaatg aagtgttcag gagttctaaa atttcatcaa atttatttag   3600
aaattgagaa atgaatttt gagtacatca acttcttcaa ttcttacaaa taatacaata   3660
aacccgtgaa taaaaacatg tatttcttat atagatttgt gacaagaaat atcacattca   3720
cttttgcttg agcatgtcca cttaagctgc tagatacgat ttttacagaa tgcaaaaagg   3780
cccaaaaatt tagaacgaca gggtcaggta acatacgaaa atccaagaga atgttgccct   3840
ctcttgttga tttacttgga aacttacact ttttatacgc tttctcacaa gttctaccaa   3900
cttaaaaccg cagttcattt tacttatact cttatgttca ttaacacttt gttcccgtat   3960
caatatcaac tttaggaacg attcacactt ggagtcactg caattctcag tatggctgtc   4020
ttatcattgg ttgttactga aaaggtacca catagttcgg aaaatgttcc actcctcagt   4080
aagttttttt tcttaagaac aaagttgatg ttttaa                              4116
```

<210> SEQ ID NO 6
<211> LENGTH: 511
<212> TYPE: PRT
<213> ORGANISM: Rattus norvegicus

<400> SEQUENCE: 6

```
Met Thr Leu Ser His Ser Ala Leu Gln Phe Trp Thr His Leu Tyr Leu
1               5                   10                  15

Trp Cys Leu Leu Leu Val Pro Ala Val Leu Thr Gln Gln Gly Ser His
            20                  25                  30

Thr His Ala Glu Asp Arg Leu Phe Lys His Leu Phe Gly Gly Tyr Asn
                35                  40                  45

Arg Trp Ala Arg Pro Val Pro Asn Thr Ser Asp Val Ile Val Arg
50                  55                  60

Phe Gly Leu Ser Ile Ala Gln Leu Ile Asp Val Asp Glu Lys Asn Gln
65                  70                  75                  80

Met Met Thr Thr Asn Val Trp Leu Lys Gln Glu Trp Asn Asp Tyr Lys
                85                  90                  95

Leu Arg Trp Asp Pro Ala Glu Phe Gly Asn Val Thr Ser Leu Arg Val
            100                 105                 110

Pro Ser Glu Met Ile Trp Ile Pro Asp Ile Val Leu Tyr Asn Asn Ala
            115                 120                 125

Asp Gly Glu Phe Ala Val Thr His Met Thr Lys Ala His Leu Phe Phe
130                 135                 140

Thr Gly Thr Val His Trp Val Pro Pro Ala Ile Tyr Lys Ser Ser Cys
145                 150                 155                 160

Ser Ile Asp Val Thr Phe Phe Pro Phe Asp Gln Gln Asn Cys Lys Met
                165                 170                 175

Lys Phe Gly Ser Trp Thr Tyr Asp Lys Ala Lys Ile Asp Leu Glu Gln
            180                 185                 190

Met Glu Arg Thr Val Asp Leu Lys Asp Tyr Trp Glu Ser Gly Glu Trp
            195                 200                 205

Ala Ile Ile Asn Ala Thr Gly Thr Tyr Asn Ser Lys Lys Tyr Asp Cys
210                 215                 220

Cys Ala Glu Ile Tyr Pro Asp Val Thr Tyr Tyr Phe Val Ile Arg Arg
225                 230                 235                 240

Leu Pro Leu Phe Tyr Thr Ile Asn Leu Ile Ile Pro Cys Leu Leu Ile
                245                 250                 255

Ser Cys Leu Thr Val Leu Val Phe Tyr Leu Pro Ser Glu Cys Gly Glu
            260                 265                 270

Lys Ile Thr Leu Cys Ile Ser Val Leu Leu Ser Leu Thr Val Phe Leu
            275                 280                 285

Leu Leu Ile Thr Glu Ile Ile Pro Ser Thr Ser Leu Val Ile Pro Leu
290                 295                 300

Ile Gly Glu Tyr Leu Leu Phe Thr Met Ile Phe Val Thr Leu Ser Ile
305                 310                 315                 320

Val Ile Thr Val Phe Val Leu Asn Val His His Arg Ser Pro Ser Thr
                325                 330                 335

His Asn Met Pro Asn Trp Val Arg Val Ala Leu Leu Gly Arg Val Pro
            340                 345                 350

Arg Trp Leu Met Met Asn Arg Pro Leu Pro Pro Met Glu Leu His Gly
            355                 360                 365

Ser Pro Asp Leu Lys Leu Ser Pro Ser Tyr His Trp Leu Glu Thr Asn
370                 375                 380

Met Asp Ala Gly Glu Arg Glu Glu Thr Glu Glu Glu Glu Glu Glu Glu
385                 390                 395                 400

Asp Glu Asn Ile Cys Val Cys Ala Gly Leu Pro Asp Ser Ser Met Gly
                405                 410                 415

Val Leu Tyr Gly His Gly Gly Leu His Leu Arg Ala Met Glu Pro Glu
            420                 425                 430
```

Thr Lys Thr Pro Ser Gln Ala Ser Glu Ile Leu Leu Ser Pro Gln Ile
            435                 440                 445

Gln Lys Ala Leu Glu Gly Val His Tyr Ile Ala Asp Arg Leu Arg Ser
450                 455                 460

Glu Asp Ala Asp Ser Ser Val Lys Glu Asp Trp Lys Tyr Val Ala Met
465                 470                 475                 480

Val Val Asp Arg Ile Phe Leu Trp Leu Phe Ile Ile Val Cys Phe Leu
                485                 490                 495

Gly Thr Ile Gly Leu Phe Leu Pro Pro Phe Leu Ala Gly Met Ile
            500                 505                 510

<210> SEQ ID NO 7
<211> LENGTH: 501
<212> TYPE: PRT
<213> ORGANISM: Fugu rubripes

<400> SEQUENCE: 7

Cys Arg Cys Ala Asp Ser Glu Glu Arg Leu Met Asn Trp Leu Leu Gly
1               5                   10                  15

Lys Asn Arg Tyr Asn Pro Leu Ile Arg Pro Ala Ser Asn Arg Thr Glu
            20                  25                  30

Arg Val Pro Val Lys Leu Gln Val Ser Leu Ala Gln Leu Ile Ser Val
        35                  40                  45

Asn Glu Arg Glu Gln Ile Met Thr Thr Asn Leu Trp Leu Met Gln His
50                  55                  60

Trp Val Asp Tyr Arg Leu Ser Trp Asp Pro Ala Lys Tyr Glu Gly Ile
65                  70                  75                  80

Asn Lys Leu Arg Ile Pro Ser Arg Leu Ile Trp Leu Pro Asp Ile Val
                85                  90                  95

Leu Tyr Asn Asn Ala Asp Gly Thr Tyr Glu Val Thr Val Phe Thr Asn
            100                 105                 110

Ala Ile Val Leu Phe Asn Gly Ser Ile Asn Trp Leu Pro Pro Ala Ile
        115                 120                 125

Tyr Lys Ser Ala Cys Lys Ile Glu Val Lys His Phe Pro Phe Asp Gln
130                 135                 140

Gln Asn Cys Thr Leu Lys Phe Arg Ser Trp Thr Tyr Asp Arg Thr Glu
145                 150                 155                 160

Ile Asp Leu Val Leu Lys Thr Asp Ala Ala Ser Met Asp Asp Phe Thr
                165                 170                 175

Pro Ser Gly Glu Trp Asp Ile Leu Ala Leu Pro Gly Arg Arg Thr Val
            180                 185                 190

Asn Pro Leu Asp Pro Thr Tyr Val Asp Leu Thr Tyr Asp Phe Ile Ile
        195                 200                 205

Lys Arg Lys Pro Leu Phe Tyr Thr Ile Asn Leu Ile Ile Pro Cys Ile
210                 215                 220

Leu Ile Thr Ser Leu Ala Ile Leu Val Phe Tyr Leu Pro Ser Asp Cys
225                 230                 235                 240

Gly Glu Lys Met Thr Leu Cys Ile Ser Val Leu Leu Ala Leu Thr Val
                245                 250                 255

Phe Leu Leu Leu Ile Ser Lys Ile Val Pro Pro Thr Ser Leu Asp Val
            260                 265                 270

Pro Leu Ile Gly Lys Tyr Leu Met Phe Thr Met Val Leu Val Thr Phe
        275                 280                 285

Ser Ile Ile Thr Ser Val Cys Val Leu Asn Val His His Arg Ser Pro
290                 295                 300

```
Ser Thr His Thr Met Pro Ser Trp Val Lys Leu Ile Phe Leu Val Lys
305                 310                 315                 320

Leu Pro Ser Leu Leu Phe Ile Arg Arg Pro Gln Asn Asn Ser Ala Arg
                325                 330                 335

Gln Arg Leu Gln Ser Gln Arg Cys Gln Arg Ala Lys Arg Asp Ile Leu
            340                 345                 350

Gly Leu Gly Cys Gln Pro Lys Ser Ser Ile Thr Met Leu Ser Ser Ala
        355                 360                 365

Leu Leu Ser Pro Gly Ser Val Phe Ser Thr Pro Gly Gln Lys Asn Val
370                 375                 380

Ala Pro Ser Leu Ser Cys Gly Tyr Gly Lys Gly Asp Leu Arg Pro Thr
385                 390                 395                 400

Thr Tyr Leu Pro Gly Gly Leu Asn Ile Thr Gln Asn Leu Gln Gln Ser
                405                 410                 415

Ser Gly Ala Asp Trp Ala Ala Asp Val Gln Glu Ala Leu Ser Gly Val
            420                 425                 430

Arg Phe Val Ala Glu His Met Met Glu Asp Asp Asp Gln Ser Val
        435                 440                 445

Ile Glu Asp Trp Lys Tyr Val Ala Met Val Val Asp Arg Met Phe Leu
                450                 455                 460

Trp Ile Phe Val Ile Val Cys Val Val Gly Thr Leu Gly Leu Phe Leu
465                 470                 475                 480

Gln Pro Val Phe Gln Asn Pro Ile Thr Pro Ile Gln Gln Pro Ser Ser
                485                 490                 495

Asp Met Pro Arg Ile
                500

<210> SEQ ID NO 8
<211> LENGTH: 783
<212> TYPE: PRT
<213> ORGANISM: Caenorhabditis elegans

<400> SEQUENCE: 8

Met Trp Ile Lys Leu Leu Phe Phe Phe Thr Thr Leu Leu Val Ser Thr
1               5                   10                  15

Ser Gly Leu Gly Asp Asp Gly Ile Thr Ala Leu Leu Asp Pro Asn Ser
                20                  25                  30

Thr Glu Phe Ser Thr Val Leu Pro Ser Asn Asn Ser Glu Lys Phe Ser
            35                  40                  45

Tyr Met Leu Ala Ser Val Lys Asn Met Asn Met Thr Ala Ser Glu Phe
        50                  55                  60

Glu Glu Phe Ile Lys Val Leu Lys His Arg Gln Ser Lys Asp His Ser
65                  70                  75                  80

Gly Glu His Val Gly Asn Glu His Asp Glu Ser His Gly Ile Ser Val
                85                  90                  95

Val Ser Trp His Trp Asp Tyr Val Lys Asn Glu Leu Val Leu Thr Leu
            100                 105                 110

Phe Phe Ile Val Ile Gly Leu Phe Lys Leu Val Tyr His His Thr Phe
        115                 120                 125

Val Thr Arg Lys Ile Leu Pro Glu Ser Cys Cys Leu Ile Phe Ile Gly
130                 135                 140

Ile Ala Ile Gly Phe Phe Val Gly Asp Ala Thr His Ala Ser Ile
145                 150                 155                 160

Lys Phe Leu Glu Phe Lys Ser Lys Val Phe Phe Tyr Leu Leu Pro
                165                 170                 175
```

```
Pro Ile Ile Leu Glu Ser Ala Tyr Ser Leu Lys Asp Arg Ala Phe Ile
            180                 185                 190

Glu Asn Ile Gly Thr Ile Leu Leu Tyr Ala Val Val Gly Thr Ile Leu
            195                 200                 205

Asn Ile Val Leu Leu Ala Ala Leu Leu Ile Leu Ile Trp Val Gly
            210                 215                 220

Ile Met Gly Lys Tyr Asn Leu Ser Val Met Asp Ile Leu Thr Phe Ala
225                 230                 235                 240

Ser Leu Val Ala Ala Val Asp Pro Val Ala Val Leu Ala Val Phe Gln
                245                 250                 255

Glu Val Gly Val Asn Lys Met Leu Tyr Phe Met Val Phe Gly Glu Ser
                260                 265                 270

Leu Phe Asn Asp Ala Val Thr Ile Val Cys Tyr Asn Leu Ala Ile Glu
                275                 280                 285

Phe Gln Thr Leu Pro Asp Phe Thr Trp Tyr His Gly Phe Leu Gly Leu
            290                 295                 300

Leu Ser Phe Leu Cys Val Ser Ile Gly Gly Leu Ile Ile Gly Leu Ile
305                 310                 315                 320

Cys Gly Ala Ile Ser Ser Phe Val Thr Lys Phe Thr Thr Asp Val Arg
                325                 330                 335

Val Val Glu Pro Val Val Leu Phe Gly Met Ala Tyr Leu Ala Tyr Leu
                340                 345                 350

Gly Ser Glu Met Phe His Phe Ser Gly Ile Ile Ala Leu Ile Ala Cys
            355                 360                 365

Gly Leu Phe Gln Thr His Tyr Ala Cys Cys Asn Ile Ser Tyr Lys Ser
            370                 375                 380

Phe Thr Ser Val Met Tyr Ile Thr Lys Val Cys Ser Thr Leu Cys Glu
385                 390                 395                 400

Ser Leu Ile Phe Ile Ile Leu Gly Val Met Leu Val Asn Glu Arg Glu
                405                 410                 415

Trp Phe Trp Thr Asp Trp His Pro Val Phe Ser Ala Val Ser Val Val
            420                 425                 430

Leu Cys Val Val Val Arg Phe Gly Val Thr Phe Phe Leu Thr Tyr Phe
            435                 440                 445

Val Asn Gln Phe Thr Gly Gly Val Arg His Ile Ser Phe Gln Glu Gln
            450                 455                 460

Phe Ile Met Ser Tyr Gly Gly Leu Arg Gly Ala Val Ser Phe Ser Leu
465                 470                 475                 480

Val Phe Met Ile Ser Ala Asn Pro Asp Val Lys Asn Thr Met Leu Gly
                485                 490                 495

Ala Thr Tyr Ala Val Ile Leu Phe Thr Asn Ile Ile Gln Gly Ser Thr
            500                 505                 510

Ile Lys Leu Phe Val Lys Trp Leu Asn Ile Arg Leu Ala Lys Lys Glu
            515                 520                 525

Asp His Phe Arg Leu Phe Ile Glu Phe Asn Asn Gly Met Val Gln His
            530                 535                 540

Leu Ser Gln Gly Ile Glu Asp Leu Cys Gly Asp Lys Ser Leu Ser Leu
545                 550                 555                 560

Ile Asn Arg Met Ser Glu Leu Ser Lys Lys Tyr Val Arg Pro Leu Leu
                565                 570                 575

Glu Lys Asn Tyr Thr Ala Asn Lys Ala Lys Lys Glu Gly Lys Leu Val
            580                 585                 590

Glu Leu Asn Arg Ala Val Ala Met Arg Glu Ala Leu Asn Asn Ser Pro
```

```
                    595                 600                 605
Ser Gln Ser Ser Phe Gln Arg Gln His Thr Ile Asp Glu Met Ala Glu
        610                 615                 620

Ser Gly Ala Leu Pro His Asp Leu Leu Asp Glu Glu His Gln Gly His
625                 630                 635                 640

His His His Gly Gln Val His Pro Asp Asn Glu Asp Ala Asp Gln Arg
                645                 650                 655

Ala Asn Glu Leu Ile Lys Asp Val Ser Ser Ile Arg Gln Leu Met His
        660                 665                 670

Asn Pro Phe Glu Asp Cys Tyr Leu Asp Arg Asn Leu Thr His Glu Glu
        675                 680                 685

Glu Lys Glu Gln Ala Arg Leu Lys Met Lys Lys Thr Arg Ala Phe Lys
        690                 695                 700

Phe Ser Ser Val Arg Lys Thr Ile Gly Phe Phe Gly Lys Lys Lys Ser
705                 710                 715                 720

Val Arg Arg His Ala Thr Gln Gln Gly Ile Leu His Ser Ala Ile Ala
                725                 730                 735

Thr Ile Gly Val Gln Ser Val Asp Arg Pro Ser Thr Ser Thr Arg Val
                740                 745                 750

Ser Val Glu Asp Glu Glu Gln Gly Leu Thr Met Lys Glu Met Glu Glu
        755                 760                 765

Glu His Pro Leu Met Thr Ile Thr Glu Ser Glu Glu Thr Ser Phe
        770                 775                 780
```